United States Patent
Stein et al.

(10) Patent No.: US 7,851,168 B2
(45) Date of Patent: Dec. 14, 2010

(54) 7A5/PROGNOSTIN AND USE THEREOF FOR THE DIAGNOSTIC AND THERAPY OF TUMORS

(75) Inventors: Ulrike Stein, Schwanebeck (DE); Holger Schwabe, Berlin (DE); Wolfgang Walther, Schwanebeck (DE); Peter Michael Schlag, Berlin (DE)

(73) Assignee: Charité-Universitaets-Medezin Berlin, Berlin (DE)

( * ) Notice: Subject to any disclaimer, the term of this patent is extended or adjusted under 35 U.S.C. 154(b) by 0 days.

(21) Appl. No.: 10/564,823

(22) PCT Filed: Jul. 19, 2004

(86) PCT No.: PCT/EP2004/008053

§ 371 (c)(1),
(2), (4) Date: Apr. 18, 2006

(87) PCT Pub. No.: WO2005/010042

PCT Pub. Date: Feb. 3, 2005

(65) Prior Publication Data

US 2006/0228370 A1    Oct. 12, 2006

(30) Foreign Application Priority Data

Jul. 18, 2003   (DE)   ................  103 32 854

(51) Int. Cl.
  *G01N 33/574*   (2006.01)
(52) U.S. Cl. ........................ 435/7.23; 435/7.1; 435/6
(58) Field of Classification Search ........................ None
  See application file for complete search history.

(56) References Cited

FOREIGN PATENT DOCUMENTS

WO    WO 02/29086    *   4/2002

OTHER PUBLICATIONS

Tockman et al (Cancer Res., 1992, 52:2711s-2718s.*
Taber's Cyclopedic Medical Dictionary, 1985, F.A. Davis Company, Philadelphia, p. 274.*
Busken, C et al, Digestive Disease Week Abstracts and Itinerary Planner, 2003, abstract No. 850.*
Kaiser, Science, 2006, 313, 1370.*
Krontiris and Capizzi, Internal Medicine, 4th Edition, Editor-in-chief Jay Stein, Elsevier Science, 1994 Chapters 71-72, pp. 699-729.*
Carter, S. K. et al. Chemotherapy of Cancer; Second edition; John Wiley & Sons: New York, 1981; appendix C.*
Database EMBL Apr. 28, 2003, International Human Genome Sequencing Consortium, "The DNA sequence of *Homo sapiens*: similar to expressed squence".
Database Geneseq Online, Feb. 25, 2003, Human liver single exon probe, Seq ID No. 20133.
Database Geneseq Online, Aug. 2, 2002, Human colon cancer related nucleotide sequence Seq ID No. 2340.
Otsuka et al., "Differential expression of the L-plastin gene in human colorectal cancer progression and metastasis", Biochemical and Biophysical Research Communications, vol. 289, 2001, pp. 876-881.
Brett et al., "A rapid bioinformatic method identifies novel genes with direct clinical relevance to colon cancer", Oncogene, vol. 20, No. 33, Jul. 27, 2001, pp. 4581-4585.
Knoesel et al., "Incidence of chromosomal imbalances in advanced colorectal carcinomas and their metastases", Virchows Archiv, vol. 440, No. 2, Feb. 2002, pp. 187-194.
Database UniProt., Online, Oct. 1, 2003, Schwabe et al, "Putative binding protein 7a5".

* cited by examiner

*Primary Examiner*—Misook Yu
*Assistant Examiner*—Mark Halvorson
(74) *Attorney, Agent, or Firm*—Saliwanchik, Lloyd & Saliwanchik

(57) ABSTRACT

The present invention refers to the nucleic acid sequence encoding for the polypeptide of 7a5/Prognostin and to its uses, in particular for the tumour diagnostics and tumour therapy of metastasising tumours.

5 Claims, 6 Drawing Sheets

Figure 3

Figure 1:
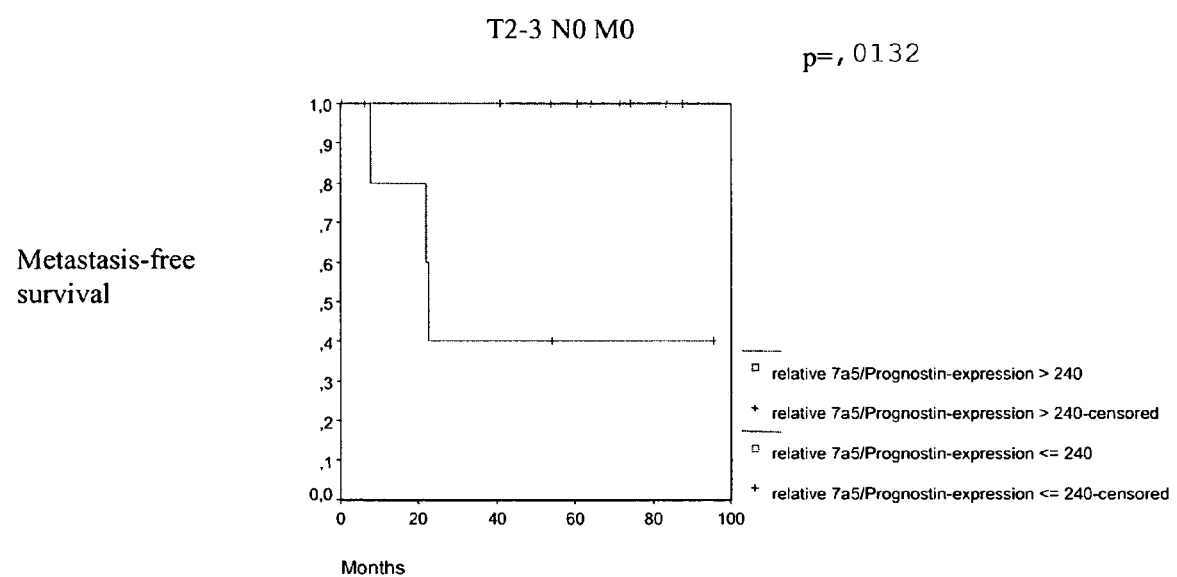

```
   1 ATGCTAATCACTGAAAGAAAACATTTTCGGTCAGGAAGAATTGCACAAAGTATGTCTGAAGCAAATTTGATTGACATGGAAGCTGGAAAACTCTCAAAAAGTTGCAATATTACAGAATGC
     M  L  I  T  E  R  K  H  F  R  S  G  R  I  A  Q  S  M  S  E  A  N  L  I  D  M  E  A  G  K  L  S  K  S  C  N  I  T  E  C
                                                                                                 NPF                    NPF
 121 CAGGACCCAGACTTGCTTCACAATTGGCCGGATGCTTTCACCCTTCGTGGTAATAATGCTTCCAAAGTTGCAAATCCATTCTGGAATCAACTGTCTGCTTCTAACCCATTTTTGGATGAC
     Q  D  P  D  L  L  H  N  W  P  D  A  F  T  L  R  G  N  N  A  S  K  V  A  N  P  F  W  N  Q  L  S  A  S  N  P  F  L  D  D

241 ATAACTCAACTAAGAAATAACAGGAAGAGAAATAATATTTCCATCTTAAAGGAAGATCCTTTTCTTTTCTGTAGAGAAATAGAAAATGGAAAATTCTTTTGATTCCTCCGGTGATGAACTT
     I  T  Q  L  R  N  N  R  K  R  N  N  I  S  I  L  K  E  D  P  F  L  F  C  R  E  I  E  N  G  N  S  F  D  S  S  G  D  E  L

361 GATGTGCATCAGTTACTTAGGCAGACTTCCTCAAGAAATTCTGGAAGATCTAAAAGTGTTTCAGAACTTCTGGACATTTTAGACGACACAGCACATGCCCATCAGAGTATACATAACTCT
     D  V  H  Q  L  L  R  Q  T  S  S  R  N  S  G  R  S  K  S  V  S  E  L  L  D  I  L  D  D  T  A  H  A  H  Q  S  I  H  N  S

481 GACCAGATCCTACTACACGACTTAGAGTGGCTTAAAAATGATCGGGAGGCTTATAAAATGGCTTGGTTAAGTCAACGCCAGCTGGCCCGCTCCTGCCTTGATTTGAATACAATTAGTCAG
     D  Q  I  L  L  H  D  L  E  W  L  K  N  D  R  E  A  Y  K  M  A  W  L  S  Q  R  Q  L  A  R  S  C  L  D  L  N  T  I  S  Q

601 AGCCCTGGATGGGCCCAGACACAACTTGCGGAGGTCACCATAGCTTGCAAAGTAAACCATCAAGGAGGGTCAGTACAATTACCTGAATCAGACATCACTGTTCATGTGCCCCAAGGTCAT
     S  P  G  W  A  Q  T  Q  L  A  E  V  T  I  A  C  K  V  N  H  Q  G  G  S  V  Q  L  P  E  S  D  I  T  V  H  V  P  Q  G  H

721 GTGGCTGTGGGAGAATTCCAAGAGGTGTCTCTAAGGGCTTTCCTTGATCCGCCACACATGCTTAACCATGATCTTCGTGCACTGTGAGCCCGTTGTTGGAAATCATGTTAGGCAACCTC
     V  A  V  G  E  F  Q  E  V  S  L  R  A  F  L  D  P  P  H  M  L  N  H  D  L  S  C  T  V  S  P  L  L  E  I  M  L  G  N  L

841 AATACAATGGAAGCCCTTTTGCTGGAGATGAAAATTGGGGCTGAAGTAAGAAAGGATCCTTTCAGCCAAGTCATGACAGAAATGGTGTGTTTACACAGCTTGGGTAAAGAAGGCCCCTTTT
     N  T  M  E  A  L  L  L  E  M  K  I  G  A  E  V  R  K  D  P  F  S  Q  V  M  T  E  M  V  C  L  H  S  L  G  K  E  G  P  F

961 AAAGTTTTAAGCAACTGCTACATTTATAAAGACACCATCCAAGTCAAGCTAATCGACTTGAGTCAGGTAATGTATCTAGTGGTTGCTGCACAAGCTAAAGCTCTTCCGTCACCAGCTGCC
     K  V  L  S  N  C  Y  I  Y  K  D  T  I  Q  V  K  L  I  D  L  S  Q  V  M  Y  L  V  V  A  A  Q  A  K  A  L  P  S  P  A  A

1081 ACCATTTGGGATTATATCCACAAAACCACCTCAATTGGAATTTATGGACCCAAATATATCCATCCCAGTTTTACTGTTGTTTTAACAGTTTGTGGACACAATTATATGCCAGGACAGCTT
     T  I  W  D  Y  I  H  K  T  T  S  I  G  I  Y  G  P  K  Y  I  H  P  S  F  T  V  V  L  T  V  C  G  H  N  Y  M  P  G  Q  L

1201 ACAATTTCTGATATTAAGAAGGGTGGAAAAAACATATCTCCAGTTGTGTTTCAGCTCTGGGGGAAGCAGTCATTTTTACTTGACAAGCCACAAGATTTAAGTATTTCTATTTTTTCCTGT
     T  I  S  D  I  K  K  G  G  K  N  I  S  P  V  V  F  Q  L  W  G  K  Q  S  F  L  L  D  K  P  Q  D  L  S  I  S  I  F  S  C

1321 GATCCTGATTTTGAAGTAAAGACAGAAGGAGAAAGGAAAGAAATTAAACAAAAGCAGTTGGAAGCAGGTGAAGTAGTTCATCAACAATTTTTATTTTCTTTAGTTGAGCACAGAGAGATG
     D  P  D  F  E  V  K  T  E  G  E  R  K  E  I  K  Q  K  Q  L  E  A  G  E  V  V  H  Q  Q  F  L  F  S  L  V  E  H  R  E  M

1441 CACTTGTTTGATTTTGTGTTCAAGTGGAGCCTCCCAATGGTGAACCAGTTGCACAGTTCTCTATCACTACTCCTGATCCAACCCCAAACCTAAAAAGACTCTCGAATCTGCCAGGCTAT
     H  L  F  D  F  C  V  Q  V  E  P  P  N  G  E  P  V  A  Q  F  S  I  T  T  P  D  P  T  P  N  L  K  R  L  S  N  L  P  G  Y
                                                                PXXP
1561 TTGCAGAAGAAGGAGGAAATCAAGTCTGCTCCTTTATCACCAAAAATTCTTGTTAAATATCCTACATTTCAAGATAAAACATTGAACTTTAGCAACTATGGGTAACCCTGAAGGCAGTG
     L  Q  K  K  E  E  I  K  S  A  P  L  S  P  K  I  L  V  K  Y  P  T  F  Q  D  K  T  L  N  F  S  N  Y  G  V  T  L  K  A  V
                                                                                                       SH3
1681 CTAAGACAAAGCAAGATTGATTACTTCCTTGAATATTTCAAAGGGGACACAATAGCTCTCCTCGGGGAAGGTAAGGTAAAAGCTATTGGTCAGTCCAAAGTGAAAGAATGGTATGTAGGA
     L  R  Q  S  K  I  D  Y  F  L  E  Y  F  K  G  D  T  I  A  L  L  G  E  G  K  V  K  A  I  G  Q  S  K  V  K  E  W  Y  V  G

1801 GTCCTCAGAGGTAAGATTGGACTTGTACACTGCAAAAATGTCAAGGTCGATTTCAAAGGAGCAAGTAATGTTTATGTCAGATAGTGTCTTTACAACCAGAAATCTTCTTGAACAGATTGTC
     V  L  R  G  K  I  G  L  V  H  C  K  N  V  K  V  I  S  K  E  Q  V  M  F  M  S  D  S  V  F  T  T  R  N  L  L  E  Q  I  V

1921 CTGCCTTTAAAAAAATTGACTTATATCTACTCAGTTGTATTAACCTTGGTGTCAGAAAAAGTTTATGATTGGAAAGTTTTAGCTGATGTCCTGGGTTACTCACATCTGTCCCTGGAAGAT
     L  P  L  K  K  L  T  Y  I  Y  S  V  V  L  T  L  V  S  E  K  V  Y  D  W  K  V  L  A  D  V  L  G  Y  S  H  L  S  L  E  D
                                                                                      Y
2041 TTTGATCAAATTCAAGCAGACAAACAATCAGACAAAGTTCTTATGTTATAAAGAAGTTAAAGGAAGATTGCCACACAGAGAGAAATACAAGGAAGTTTCTGTATGAACTTATTGTGGCT
     F  D  Q  I  Q  A  D  K  E  S  E  K  V  S  Y  V  I  K  K  L  K  E  D  C  H  T  E  R  N  T  R  K  F  L  Y  E  L  I  V  A

2161 CTTCTGAAAATGGATTGCCAAGAGTTAGTCGCACGTCTCATCCAAGAAGCTGCTGTTCTGACTTCAGCTGTCAAGCTTGGAAAAGGCTGGAGGGAACTAGCTGAAAAGTTAGTACGACTC
     L  L  K  M  D  C  Q  E  L  V  A  R  L  I  Q  E  A  A  V  L  T  S  A  V  K  L  G  K  G  W  R  E  L  A  E  K  L  V  R  L
                                                                                                        Y
2281 ACAAAGCAACAAATGGAGGCATATGAAATTCCTCATCGAGGAAACACTGGAGATGTTGCTGTTGAGATGATGTGGAAACCTGCCTATGATTTTCTGTATACCTGGAGTGCTCACTATGGA
     T  K  Q  Q  M  E  A  Y  E  I  P  H  R  G  N  T  G  D  V  A  V  E  M  M  W  K  P  A  Y  D  F  L  Y  T  W  S  A  H  Y  G

2401 AATAACTACAGAGATGTTACAAGACCTTCAGTCAGCTTTGGACAGAATGAAAAACCCTGTGACTAAACACTGGAGAGAATTAACTGGAGTTTTAATACTAGTAAATTCTTTGGAGGTT
     N  N  Y  R  D  V  L  Q  D  L  Q  S  A  L  D  R  M  K  N  P  V  T  K  H  W  R  E  L  T  G  V  L  I  L  V  N  S  L  E  V

2521 TTGAGAGTAACTGCATTCTCCACTTCTGAGGAAGTATAG
     L  R  V  T  A  F  S  T  S  E  E  V  *
```

Figure 6
A
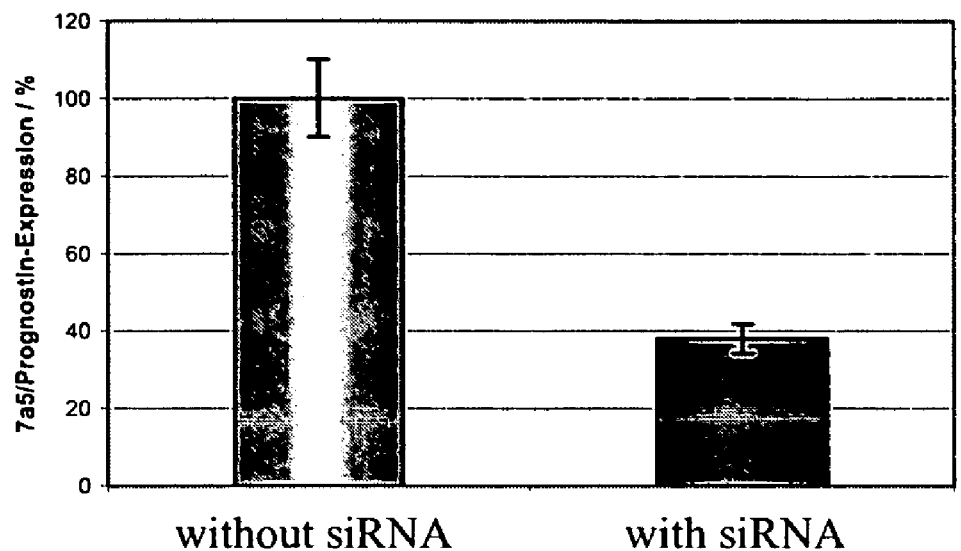
B
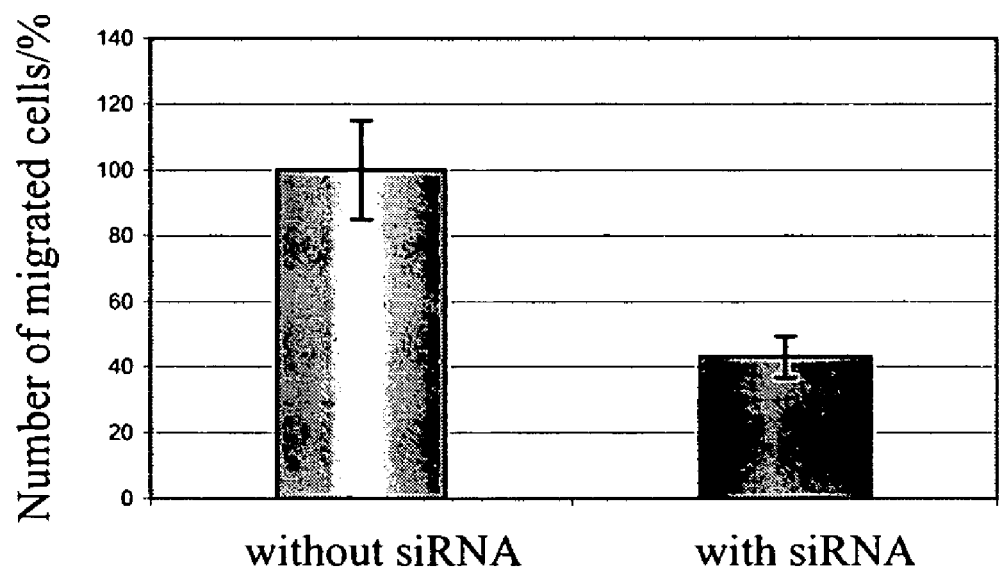

SEQUENCE LISTING

<160> NUMBER OF SEQ ID NOS: 8

<210> SEQ ID NO 1
<211> LENGTH: 2559
<212> TYPE: DNA
<213> ORGANISM: Homo sapiens

<400> SEQUENCE: 1

```
atgctaatca ctgaaagaaa acattttcgg tcaggaagaa ttgcacaaag tatgtctgaa     60
gcaaatttga ttgacatgga agctggaaaa ctctcaaaaa gttgcaatat tacagaatgc    120
caggacccag acttgcttca caattggccg gatgctttca cccttcgtgg taataatgct    180
tccaaagttg caaatccatt ctggaatcaa ctgtctgctt ctaacccatt tttggatgac    240
ataactcaac taagaaataa caggaagaga aataatattt ccatcttaaa ggaagatcct    300
tttcttttct gtagagaaat agaaaatgga aattcttttg attcctccgg tgatgaactt    360
gatgtgcatc agttacttag gcagacttcc tcaagaaatt ctggaagatc taaaagtgtt    420
tcagaacttc tggacatttt agacgacaca gcacatgccc atcagagtat acataactct    480
gaccagatcc tactacacga cttagagtgg cttaaaaatg atcgggaggc ttataaaatg    540
gcttggttaa gtcaacgcca gctggcccgc tcctgccttg atttgaatac aattagtcag    600
agccctggat gggcccagac acaacttgcg gaggtcacca tagcttgcaa agtaaaccat    660
caaggagggt cagtacaatt acctgaatca gacatcactg ttcatgtgcc ccaaggtcat    720
gtggctgtgg gagaattcca agaggtgtct ctaagggctt tccttgatcc gccacacatg    780
cttaaccatg atctttcgtg cactgtgagc ccgttgttgg aaatcatgtt aggcaacctc    840
aatacaatgg aagccctttt gctggagatg aaaattgggg ctgaagtaag aaaggatcct    900
ttcagccaag tcatgacaga aatggtgtgt ttacacagct tgggtaaaga aggccctttt    960
aaagttttaa gcaactgcta catttataaa gacaccatcc aagtcaagct aatcgacttg   1020
agtcaggtaa tgtatctagt ggttgctgca caagctaaag ctcttccgtc accagctgcc   1080
accatttggg attatatcca caaaaccacc tcaattggaa tttatggacc caaatatatc   1140
catcccagtt ttactgttgt tttaacagtt tgtggacaca attatatgcc aggacagctt   1200
acaatttctg atattaagaa gggtggaaaa aacatatctc cagttgtgtt tcagctctgg   1260
gggaagcagt cattttact tgacaagcca caagatttaa gtatttctat ttttcctgt   1320 gatcctgatt ttgaagtaaa gacagaagga gaaggaaag aaattaaaca aaagcagttg   1380
gaagcaggtg aagtagttca tcaacaattt ttattttctt tagttgagca cagagagatg   1440
cacttgtttg atttttgtgt tcaagtggag cctcccaatg tgaaccagt tgcacagttc   1500 tctatcacta ctcctgatcc aacccaaac ctaaaagac tctcgaatct gccaggctat   1560
ttgcagaaga aggaggaaat caagtctgct cctttatcac caaaaattct tgttaaatat   1620
cctacatttc aagataaaac attgaacttt agcaactatg gggtaaccct gaaggcagtg   1680
ctaagacaaa gcaagattga ttacttcctt gaatatttca aaggggacac aatagctctc   1740
```

```
ctcggggaag gtaaggtaaa agctattggt cagtccaaag tgaaagaatg gtatgtagga    1800
gtcctcagag gtaagattgg acttgtacac tgcaaaaatg tcaaggtgat ttcaaaggag    1860
caagtaatgt ttatgtcaga tagtgtcttt acaaccagaa atcttcttga acagattgtc    1920
ctgcctttaa aaaaattgac ttatatctac tcagttgtat taaccttggt gtcagaaaaa    1980
gtttatgatt ggaaagtttt agctgatgtc ctgggttact cacatctgtc cctgaagat     2040 tttgatcaaa ttcaagcaga caaagaatca gagaaagttt cttatgttat aaagaagtta    2100
aaggaagatt gccacacaga gagaaataca aggaagtttc tgtatgaact tattgtggct    2160
cttctgaaaa tggattgcca agagttagtc gcacgtctca tccaagaagc tgctgttctg    2220
acttcagctg tcaagcttgg aaaaggctgg agggaactag ctgaaaagtt agtacgactc    2280
acaaagcaac aaatggaggc atatgaaatt cctcatcgag aaacactgg agatgttgct     2340 gttgagatga tgtggaaacc tgcctatgat tttctgtata cctggagtgc tcactatgga    2400
aataactaca gagatgtgtt acaagacctt cagtcagctt tggacagaat gaaaaaccct    2460
gtgactaaac actggagaga attaactgga gttttaatac tagtaaattc tttggaggtt    2520
ttgagagtaa ctgcattctc cacttctgag gaagtatag                           2559
```

<210> SEQ ID NO 2
<211> LENGTH: 852
<212> TYPE: PRT
<213> ORGANISM: Homo sapiens

<400> SEQUENCE: 2

```
Met Leu Ile Thr Glu Arg Lys His Phe Arg Ser Gly Arg Ile Ala Gln
1               5                   10                  15

Ser Met Ser Glu Ala Asn Leu Ile Asp Met Glu Ala Gly Lys Leu Ser
                20                  25                  30

Lys Ser Cys Asn Ile Thr Glu Cys Gln Asp Pro Asp Leu Leu His Asn
            35                  40                  45

Trp Pro Asp Ala Phe Thr Leu Arg Gly Asn Asn Ala Ser Lys Val Ala
        50                  55                  60

Asn Pro Phe Trp Asn Gln Leu Ser Ala Ser Asn Pro Phe Leu Asp Asp
65                  70                  75                  80

Ile Thr Gln Leu Arg Asn Asn Arg Lys Arg Asn Ile Ser Ile Leu
                85                  90                  95

Lys Glu Asp Pro Phe Leu Phe Cys Arg Glu Ile Glu Asn Gly Asn Ser
            100                 105                 110

Phe Asp Ser Ser Gly Asp Glu Leu Asp Val His Gln Leu Leu Arg Gln
        115                 120                 125

Thr Ser Ser Arg Asn Ser Gly Arg Ser Lys Ser Val Ser Glu Leu Leu
    130                 135                 140

Asp Ile Leu Asp Asp Thr Ala His Ala His Gln Ser Ile His Asn Ser
145                 150                 155                 160

Asp Gln Ile Leu Leu His Asp Leu Glu Trp Leu Lys Asn Asp Arg Glu
                165                 170                 175

Ala Tyr Lys Met Ala Trp Leu Ser Gln Arg Gln Leu Ala Arg Ser Cys
            180                 185                 190

Leu Asp Leu Asn Thr Ile Ser Gln Ser Pro Gly Trp Ala Gln Thr Gln
        195                 200                 205

Leu Ala Glu Val Thr Ile Ala Cys Lys Val Asn His Gln Gly Gly Ser
    210                 215                 220
```

```
Val Gln Leu Pro Glu Ser Asp Ile Thr Val His Val Pro Gln Gly His
225                 230                 235                 240

Val Ala Val Gly Glu Phe Gln Glu Val Ser Leu Arg Ala Phe Leu Asp
                245                 250                 255

Pro Pro His Met Leu Asn His Asp Leu Ser Cys Thr Val Ser Pro Leu
            260                 265                 270

Leu Glu Ile Met Leu Gly Asn Leu Asn Thr Met Glu Ala Leu Leu Leu
        275                 280                 285

Glu Met Lys Ile Gly Ala Glu Val Arg Lys Asp Pro Phe Ser Gln Val
    290                 295                 300

Met Thr Glu Met Val Cys Leu His Ser Leu Gly Lys Glu Gly Pro Phe
305                 310                 315                 320

Lys Val Leu Ser Asn Cys Tyr Ile Tyr Lys Asp Thr Ile Gln Val Lys
                325                 330                 335

Leu Ile Asp Leu Ser Gln Val Met Tyr Leu Val Ala Ala Gln Ala
            340                 345                 350

Lys Ala Leu Pro Ser Pro Ala Ala Thr Ile Trp Asp Tyr Ile His Lys
        355                 360                 365

Thr Thr Ser Ile Gly Ile Tyr Gly Pro Lys Tyr Ile His Pro Ser Phe
    370                 375                 380

Thr Val Leu Thr Val Cys Gly His Asn Tyr Met Pro Gly Gln Leu
385                 390                 395                 400

Thr Ile Ser Asp Ile Lys Lys Gly Gly Lys Asn Ile Ser Pro Val Val
                405                 410                 415

Phe Gln Leu Trp Gly Lys Gln Ser Phe Leu Leu Asp Lys Pro Gln Asp
            420                 425                 430

Leu Ser Ile Ser Ile Phe Ser Cys Asp Pro Asp Phe Glu Val Lys Thr
        435                 440                 445

Glu Gly Glu Arg Lys Glu Ile Lys Gln Lys Gln Leu Glu Ala Gly Glu
    450                 455                 460

Val Val His Gln Gln Phe Leu Phe Ser Leu Val Glu His Arg Glu Met
465                 470                 475                 480

His Leu Phe Asp Phe Cys Val Gln Val Glu Pro Pro Asn Gly Glu Pro
                485                 490                 495

Val Ala Gln Phe Ser Ile Thr Thr Pro Asp Pro Thr Pro Asn Leu Lys
            500                 505                 510

Arg Leu Ser Asn Leu Pro Gly Tyr Leu Gln Lys Lys Glu Glu Ile Lys
        515                 520                 525

Ser Ala Pro Leu Ser Pro Lys Ile Leu Val Lys Tyr Pro Thr Phe Gln
    530                 535                 540

Asp Lys Thr Leu Asn Phe Ser Asn Tyr Gly Val Thr Leu Lys Ala Val
545                 550                 555                 560

Leu Arg Gln Ser Lys Ile Asp Tyr Phe Leu Glu Tyr Phe Lys Gly Asp
                565                 570                 575

Thr Ile Ala Leu Leu Gly Glu Gly Lys Val Lys Ala Ile Gly Gln Ser
            580                 585                 590

Lys Val Lys Glu Trp Tyr Val Gly Val Leu Arg Gly Lys Ile Gly Leu
        595                 600                 605

Val His Cys Lys Asn Val Lys Val Ile Ser Lys Glu Gln Val Met Phe
    610                 615                 620

Met Ser Asp Ser Val Phe Thr Thr Arg Asn Leu Leu Glu Gln Ile Val
625                 630                 635                 640

Leu Pro Leu Lys Lys Leu Thr Tyr Ile Tyr Ser Val Val Leu Thr Leu
```

645                 650                 655
Val Ser Glu Lys Val Tyr Asp Trp Lys Val Leu Ala Asp Val Leu Gly
            660                 665                 670

Tyr Ser His Leu Ser Leu Glu Asp Phe Asp Gln Ile Gln Ala Asp Lys
            675                 680                 685

Glu Ser Glu Lys Val Ser Tyr Val Ile Lys Lys Leu Lys Glu Asp Cys
            690                 695                 700

His Thr Glu Arg Asn Thr Arg Lys Phe Leu Tyr Glu Leu Ile Val Ala
705                 710                 715                 720

Leu Leu Lys Met Asp Cys Gln Glu Leu Val Ala Arg Leu Ile Gln Glu
                725                 730                 735

Ala Ala Val Leu Thr Ser Ala Val Lys Leu Gly Lys Gly Trp Arg Glu
            740                 745                 750

Leu Ala Glu Lys Leu Val Arg Leu Thr Lys Gln Gln Met Glu Ala Tyr
            755                 760                 765

Glu Ile Pro His Arg Gly Asn Thr Gly Asp Val Ala Val Glu Met Met
            770                 775                 780

Trp Lys Pro Ala Tyr Asp Phe Leu Tyr Thr Trp Ser Ala His Tyr Gly
785                 790                 795                 800

Asn Asn Tyr Arg Asp Val Leu Gln Asp Leu Gln Ser Ala Leu Asp Arg
                805                 810                 815

Met Lys Asn Pro Val Thr Lys His Trp Arg Glu Leu Thr Gly Val Leu
            820                 825                 830

Ile Leu Val Asn Ser Leu Glu Val Leu Arg Val Thr Ala Phe Ser Thr
            835                 840                 845

Ser Glu Glu Val
    850

<210> SEQ ID NO 3
<211> LENGTH: 21
<212> TYPE: DNA
<213> ORGANISM: Homo sapiens

<400> SEQUENCE: 3
ttcttttgat tcctccggtg a                                                   21

<210> SEQ ID NO 4
<211> LENGTH: 20
<212> TYPE: DNA
<213> ORGANISM: Homo sapiens

<400> SEQUENCE: 4
actctgatgg gcatgtgctg                                                     20

<210> SEQ ID NO 5
<211> LENGTH: 32
<212> TYPE: DNA
<213> ORGANISM: Homo sapiens

<400> SEQUENCE: 5
gcagacttcc tcaagaaatt ctggaagatc ta                                       32

<210> SEQ ID NO 6
<211> LENGTH: 32
<212> TYPE: DNA
<213> ORGANISM: Homo sapiens

<400> SEQUENCE: 6

-continued

```
agtgtttcag aacttctgga cattttagac ga                              32
```

<210> SEQ ID NO 7
<211> LENGTH: 21
<212> TYPE: DNA
<213> ORGANISM: Homo sapiens

<400> SEQUENCE: 7

```
aagcttggaa aaggctggag g                                          21
```

<210> SEQ ID NO 8
<211> LENGTH: 18
<212> TYPE: PRT
<213> ORGANISM: Homo sapiens

<400> SEQUENCE: 8

```
Lys Leu His Ser Ala Leu Asp Arg Met Lys Asn Pro Val Thr Lys His
1               5                   10                  15

Trp Arg
```

7A5/PROGNOSTIN AND USE THEREOF FOR THE DIAGNOSTIC AND THERAPY OF TUMORS

CROSS REFERENCE TO RELATED APPLICATION

This application is a 35 USC §371 National Phase Entry Application from PCT/EP2004/008053, filed Jul. 19, 2004, and designating the United States.

The present invention refers to the nucleic acid sequence encoding for the polypeptide of 7a5/Prognostin and its uses, in particular for the diagnostics and therapy of metastasising tumours. For the purposes of the present invention all the references cited in this specification are completely taken into reference by quotation.

DESCRIPTION

The formation of metastases is a complex multistage process, which comprises a multiplicity of molecular and cellular changes and which can in principle be subdivided into four defined phases: a) Growth and vascularisation of the primary tumour, b) release and intrusion of single invasive cells into the vascular system, c) dissemination within the vascular system and extravasation at the target organ, and finally d) formation of macro-metastases from the invaded tumour cells.

In this process, specific cells of a primary tumour lose their cell-cell-contact, invade through the extracellular matrix and spread via the blood and the lymphatic system. These tumour cells can finally extravade, attach themselves at specific target organs and proliferate there, leading to the formation of metastases.

A group of molecules showing a general association with metastatic spread had already been identified in the comparison between the primary tumour and the metastasis. Thus, the dysregulation of cell adhesion molecules (e.g. cadherines) in the primary tumours leads to a loss of the cell-cell contact and allows the mobilised tumour cells to invade and intrude into the blood and lymphatic vascular system. Tumour cells spread via the blood and the lymphatic vascular system will then attach themselves to the endothelial cells of the vessels, which process is mediated by adhesion molecules on the endothelial cells (e.g. E-Selectin, LP AM, VCAM-1, LuE-CAM-1, ICAM-1), to which specific surface molecules of the tumour cells (e.g. VLA-4, LFA-1) can bind to in a selective manner. In the further process of metastatic spread there has to be a binding of the metastasising tumour cells to the components of the extracellular matrix, e.g. to laminin, collagens, fibronectin and vitronectin. This is mediated by different integrins, thus tumour cells with different metastasising potential vary in their adhesion to the different elements of the extracellular matrix. Also of a great importance for the extravasation and migration of the tumour cells are the matrix-degrading enzymes, e.g. the matrix-metalloproteinases (MMPs, especially MMP-9 and MMP-2) in the system with their tissue inhibitors (tissue inhibitors of MMPs, TIMPs). The activity of these molecules can be regulated via the system urokinase-type-plasminogen activator/urokinase-type-plasminogen activator receptor (uPA/uPA receptor) in a tissue specific manner, which has been shown e.g. for the expression of MMP-9 in liver metastases of colorectal carcinomas.

Essential for the adhesion of metastasising tumour cells at the target organs again are specific adhesion molecules (VCAM-1, LPAM, E-Selectin, VLAs, ICAM-1 and different integrins) [see e.g. Streit M et al., Adhesion receptors in malignant transformation and dissemination of gastrointestinal tumours. Recent Results Cancer Res. 1996; 142:19-50. Imai K, et al. Regulation of integrin function in the metastasis of colorectal cancer, Nippon Geka Gakkai Zasshi. July 1998; 99(7):415-8. Krause T, Turner G. A. Are selectins involved in metastasis? Clin Exp Metastasis. May 1999; 17(3):183-92, and Portera C. A. Jr, et al. Molecular determinants of colon cancer metastasis. Surg Oncol. November-December 1998; 7(3-4):183-95]. The tumour cells have to find a specific micro-environment at the target organs of metastatic spread to be able to adhere and proliferate ("seed and soil hypotheses") Tumour cells can first spread in the whole body, but finally generate metastases only in specific organs. The essential factor of metastatic spread thus is not the migration of the tumour cells to the target organs, but the potential of the tumour cells to proliferate in a specific environment in the target organ. "Dormant" tumour cells may exist in the body for several years without metastases being detectable.

The above described "seed and soil" hypothesis is one of the best accepted theories for organ-specific metastatic spread. Besides, there exists a second theory according to which endothelial cells express specific adhesion molecules in the blood vessels of the target organs of metastatic spread, which leads to the adhesion of circulating tumour cells and thus to the formation of metastases in theses specific organs. The third, so-called chemo-attraction theory states that organ-specific molecules enter the blood stream, where they induce tumour cells to migrate to the respective target organs of metastatic spread and to form metastases at these sites.

The present investigations in the field of organ-specific metastatic spread demonstrate, that there obviously are genes, which have to be selectively activated (or deactivated) in a longer process, which—at the time of the tumour cell spread in the body—were not active yet (or still active). Thus, analyses of gene expression are indispensable in order to investigate which genes are expressed in a different manner in the metastases of specific target organs in comparison to the respective primary tumours.

Each year about 20,000 new cases of the colon carcinoma are registered in Germany. The colon carcinoma has several known target sites of metastatic spread, e.g. the liver, lymph nodes, lung, bones and the brain.

The Robert-Rössle-Klinik is an oncologically orientated health centre with a main focus on surgery. Each year about 300 patients with colon carcinomas are treated, of which about 150-170 patients show metastases of the primary tumour. The observed metastatic frequency of the target organs is consistent with the data given in literature with 80% of liver metastases and 15% of pulmonary metastases. The 5 year-survival rate is about 20-25%, in the case of solitary metastases (liver, lung) however it is just about 5%.

The liver constitutes the most important target organ for the metastatic spread of the colon carcinoma, since the tumour cells, mediated by the portal vein, are first captured within the liver after which they disseminate to other organs.

On the other hand, it is also known that there often are metastases e.g. in the lung or in the bone without metastases being detected in the liver. Thus the metastasising colon carcinoma constitutes an interesting model for the identification and analysis of genes in order to further investigate the differential gene expression in organ-specific metastatic spread.

The proteins encoded by such genes might have a direct function in the adhesion of tumour cells at specific tissues and organs (organ-specific adhesion molecules). Furthermore, they might enable cell proliferation and metastatic growth in a specific environment by an interaction with the normal cells of the target organs (e.g. specific receptors and effectors). It is moreover conceivable, that such proteins are required for the tumour cells' intracellular preparation for their metastatic growth in a specific target organ, e.g. in different signal transduction cascades and regulatory mechanisms. Important in this context are proteins with respective protein-protein interaction domains, e.g. with Src-homology domains (SH3-, SH2-domains) or Eps15-homology domains (EH-domains). These domains are defined sequence motifs enabling a specific binding to ligands. SH3-domains, are—among other examples—present in such proteins, which direct specific ligands to kinases or their substrates and which thus play a crucial role in the regulation of tyrosine kinase signal transduction pathways.

Especially valuable is the identification of such marker genes, the expression of which in primary carcinoma cells can be employed to forecast a presumptive formation of metastases in specific target organs before the actual metastatic spread and, based thereon, a possible prevention of this process.

It is thus an object of the present invention to provide such further marker genes, by means of which one is allowed to achieve an improved diagnosis and therapy in respect of the formation of metastases in specific target organs.

According to a first aspect of the present invention, this object is achieved by the providence of a nucleic acid sequence coding for the polypeptide of 7a5/Prognostin, selected from the group: a) a nucleic acid sequence with the sequence given in SEQ ID No: 1, b) nucleic acid sequences derived from the nucleic acid sequence given in SEQ ID No: 1 as a result of the degenerated genetic code, c) derivatives of the nucleic acid sequence given in SEQ ID No: 1, which are coding for the polypeptides with the amino acid sequence given in SEQ ID No: 2 and display at least 80% of homology at the amino acid level without the biological activity of the polypeptides being significantly reduced, and d) a human genomic nucleic acid sequence, which comprises the gene for 7a5/Prognostin and displays polymorphisms. A further aspect relates to the also provided 7a5/Prognostin-polypeptide encoded by a nucleic acid sequence according to the invention, especially in conformity with the amino acid sequence of the SEQ ID No: 2.

Moreover added for the purification of the polypeptides according to the invention may be a further polypeptide ("tag"). Protein-tags e.g. allow for the high affinity adsorption to a matrix and stringent washing with suitable buffers without eluting the complex in significant amounts, followed by the purposeful elution of the adsorbed complex. Examples for protein-tags familiar to the expert are the $(His)_6$-tag, the V5-tag, the Myc-tag, the FLAG-tag, the Strep-tag, the Strep-tag II, the haemagglutinin-tag, the glutathione transferase-tag (GST)-tag, intein with an affinity-chitin-binding-tag or the maltose binding protein (MBP)-tag. These protein-tags may be located N-terminally, C-terminally and/or internally.

Apart from the natural polypeptides isolated from cells, all polypeptides according to the invention or their parts may have been produced under cell-free conditions, e.g. by synthesis or by in vitro-translation. Thus, the complete polypeptide or parts thereof may e.g. be synthesised by means of the classical synthesis (Merrifield technique). Parts of the polypeptides according to the invention are especially suitable for the generation of antisera, by means of which respective gene expression libraries can be screened in order to obtain further functional variants of the polypeptide according to the invention.

Apart from the natural nucleic acids isolated from cells, all nucleic acids according to the invention or their parts may have also been produced synthetically. Moreover one may use a synthetically produced nucleic acid to carry out the invention. Thus, the nucleic acid according to the invention may be synthesised e.g. chemically starting from the protein sequences described in SEQ ID No. 2 by employing the genetic code, this synthesis e.g. being accomplished according to the phosphotriester method (see e.g. Uhlmann & Peyman 1990, Chemical Reviews 90:543-584).

The accession number XP_294213.1 (entry into the database at Apr. 28, 2003) describes a human polypeptide with a length of 816 amino acids. This sequence described as being similar to the EST AI594717 [*Homo sapiens*] is identical to the SEQ ID No. 2 in its last 813 amino acids and was obtained from the NCBI contig NT_007819 by means of an automated computer analysis using the program "GenomeScan". The gene is localised on chromosome 7. Neither a function nor a prognostic value is known for this gene. The present invention thus provides the identification of the genomic DNA-sequence, the full length-cDNA and the putative protein sequence for 7a5/Prognostin.

A further aspect of the invention refers to an oligonucleotide, which specifically hybridises to a nucleic acid sequence according to the present invention. Oligonucleotides constitute important means, which can one the one hand be used in PCR reactions, but also as probes in hybridisation reactions. Further possible applications are to be found as therapeutic agents e.g. in gene therapy or in techniques of mutagenesis. The oligonucleotides according to the invention can be present in the form of nucleic acids comprising DNA, dsDNA, RNA, mRNA, siRNA, PNA and/or CNA. The oligonucleotides may furthermore be present as "sense" or "antisense"-oligonucleotides. For detection techniques based on hybridisation, the oligonucleotides may furthermore be appropriately labelled, e.g. by means of dyes, radionuclides, enzymes or markers of mass and charge. The labelling is dependent on the actual detection method to be employed. The oligonucleotides according to the invention are preferably a DNA, in particular a double-stranded DNA having a length of at least 8 nucleotides, preferably of at least 12 nucleotides, especially of at least 24 nucleotides. The upper limit for the oligonucleotides is determined by the actual practical use, wherein usually maximal lengths of 50-200 nucleotides are preferred.

Oligonucleotides are usually rapidly degraded by endo- or exonucleases, in particular by DNases and RNases being present in the cell. It is thus advantageous to modify the nucleic acid in order to stabilise it against degradation, so that a high concentration of the nucleic acid will be maintained over a long period in the cell (Beigelmann et al. 1995, Nucleic Acids Res. 23:3989-94; Dudycz 1995, WO 95/11910; Macadam et al. 1998, WO 98/37240; Reese et al. 1997, WO 97/29116). Typically, such a stabilisation can be achieved by the introduction of one or more internucleotide-phosphate groups or by the introduction of one or more non-phosphor-internucleotides.

Suitable modified internucleotides are summarised in Uhlmann and Peymann (1990, Chem. Rev. 90:544) (see also: Beigelman et al. 1995, Nucleic Acids Res. 23:3989-94; Dudycz 1995, WO 95/11910; Macadam et al. 1998, WO 98/37240; Reese et al. 1997, WO 97/29116). Modified internucleotide phosphate moieties and/or non-phosphor ester bonds in a nucleic acid, which may be employed in an application according to the invention, e.g. comprise methyl phosphonate, phosphorothioate, phosphoramidate, phosphorodithioate, phosphate ester, whereas non-phosphor internucleotide analogues comprise e.g. siloxane bridges, carbonate bridges, carboxymethyl ester, acetamidate bridges and/or sulphur bridges. Moreover it is intended, that this modification improves the durability of a pharmaceutical composition which can be used in one of the applications according to the invention.

For the expression of the respective gene, in general a double-stranded DNA is preferred, whereas the DNA region coding for the polypeptide is particularly preferred. This region starts at the first start codon (ATG) being located in a Kozak consensus sequence (Kozak 1987, Nucleic Acids Res. 15:8125-48) and extends to the next stop codon (TAG, TGA or TAA) being in the same reading frame as the ATG. A further application of the nucleic acid sequences according to the invention is the construction of antisense oligonucleotides (Zheng and Kemeny 1995, Clin. Exp. Immunol. 100:380-382; Nellen and Lichtenstein 1993, Trends Biochem. Sci. 18:419-23) and/or ribozymes (Amarzguioui et al. 1998, Cell. Mol. Life Sci. 54:1175-202; Vaish, et al. 1998, Nucleic Acids Res. 26:5237-42; Persidis 1997, Nat. Biotechnol. 15:921-2; Couture and Stinchcomb 1996, Trends Genet. 12:510-5). By means of "antisense"-oligonucleotides one can reduce the stability of the nucleic acid according to the invention and/or inhibit its translation. Thus, it is possible to reduce the expression of the respective genes in cells both in vivo and in vitro. Oligonucleotides may therefore be suitable as a therapeutic agent. For the application as a probe or as an "antisense"-oligonucleotide, a single-stranded DNA or RNA is preferred. The oligonucleotides according to the invention may be present in the form of nucleic acids comprising DNA, dsDNA, RNA, mRNA, siRNA, PNA and/or CNA. A further, particularly preferred aspect of the present invention refers to oligonucleotides as a therapeutic agent in the form of siRNA. This approach of gene therapy is familiar to the expert also in tumour therapy and can e.g. be gathered from the following literature and the further references cited therein. The general technical background is e.g. described in Ait-Si-Ali S, Guasconi V, Harel-Bellan A. RNA interference and its possible use in cancer therapy. Bull Cancer. January 2004; 91(1):15-8; Caplen N J, Mousses S. Short interfering RNA (siRNA)-mediated RNA interference (RNAi) in human cells. Ann NY Acad Sci. December 2003; 1002:56-62; Caplen N J RNAi as a gene therapy approach. Expert Opin Biol Ther. July 2003; 3(4):575-86; Lu P Y, Xie F Y, Woodle M C. siRNA-mediated antitumourigenesis for drug target validation and therapeutics. Curr Opin Mol Ther. June 2003; 5(3)225-34; and Oshiumi H, Begum N A, Matsumoto M, Seya T. RNA interference for mammalian cells. Nippon Yakurigaku Zasshi. August 2002; 120(2):91-5. Information concerning specific vectors for siRNA therapy can be found in Devroe E, Silver P A. Therapeutic potential of retroviral RNAi vectors. Expert Opin Biol Ther. March 2004; 4(3):319-27. Devroe E, Silver P A. Retrovirus-delivered siRNA. BMC Biotechnol. Aug. 28, 2002; 2(1):15. Tran N, Cairns M J, Dawes I W, Arndt G M. Expressing functional siRNAs in mammalian cells using convergent transcription. BMC Biotechnol. Nov. 6, 2003; 3(1):21. Futami T, Miyagishi M, Seki M, Taira K. Induction of apoptosis in HeLa cells with siRNA expression vector targeted against bcl-2. Nucleic Acids Res Suppl. 2002; (2):251-2. Scherr M, Battmer K, Ganser A, Eder M. Modulation of gene expression by lentiviral-mediated delivery of small interfering RNA. Cell Cycle. May-June 2003; 2(3):251-7. Shen C, Reske S N. Adenovirus-delivered siRNA. Methods Mol Biol. 2004; 252:523-32. Salmons B, Gunzberg W H. Targeting of retroviral vectors for gene therapy. Hum Gene Ther. April 1993; 4(2):129-41, and Kobayashi N, Matsui Y, Kawase A, Hirata K, Miyagishi M, Taira K, Nishikawa M, Takakura Y. Vector-based in vivo RNA interference: dose- and time-dependent suppression of transgene expression. J Pharmacol Exp Ther. February 2004; 308(2):668-93. Epub Nov. 10, 2003. Finally Naito Y, Yamada T, Ui-Tei K, Morishita S, Saigo K. siDirect: highly effective, target-specific siRNA design software for mammalian RNA interference. Nucleic Acids Res. Jul. 1, 2004; 32(Web Server issue): W124-9 exemplarily describe a program for the design and construction of siRNA molecules.

A further aspect of the present invention refers to the nucleic acid molecule according to the invention, the polypeptide according to the invention or to the oligonucleotide according to the invention for the treatment of diseases. The possibility to use these substances in the context with human diseases was unknown up to now.

A further aspect of the present invention refers to a vector, preferably, in the form of a plasmid, shuttle vector, phagemid, cosmid, expression vector, adenoviral vector, retroviral vector (Miller, et al. "Improved retroviral vectors for gene transfer and expression", BioTechniques Vol. 7, No. 9, p 980, 1989) and/or a gene therapeutically effective vector containing a nucleic acid according to the invention. Thus, the nucleic acid according to the invention may be contained in a vector, preferably in an expression vector or a gene therapeutically effective vector. It is preferred, that the gene therapeutically effective vector comprises cell specific regulatory sequences, which are functionally linked to the nucleic acid according to the invention. The expression vectors may be prokaryotic or eukaryotic expression vectors. Examples for prokaryotic expression vectors for the expression in *E. coli* e.g. are the vectors pGEM or pUC-derivatives, for eukaryotic expression vectors for the expression in *Saccharomyces cerevisiae* e.g. the vectors p426Met25 or p426GAL1 (Mumberg et al. 1994, Nucleic Acids Res. 22:5767-5768), for the expression in insect cells e.g. *Baculovirus*-vectors like those disclosed in the EP-B1-0 127 839 or EP-B1-0 549 721, and for the expression in mammalian cells e.g. the vectors Rc/CMV and Rc/RSV or SV40-vectors, which are all commonly available.

In general, the expression vectors also comprise promoters suitable for the respective host cell like e.g. the trp-promoter for the expression in *E. coli* (see e.g. EP-B1-0 154 133), the Met 25, GAL 1 or ADH2-promoter for the expression in yeasts (Russel et al. 1983, J. Biol. Chem. 258:2674-2682), the Baculovirus polyhedrin-promoter for the expression in insect cells (see e.g. EP-B1-0 127 839). Suitable for the expression in mammalian cells e.g. are promoters allowing for a constitutive, controllable, tissue specific, cell cycle specific, or metabolically specific expression in eukaryotic cells. Controllable elements according to the present invention are promoters, activator sequences, enhancers, silencers and/or repressor sequences. Examples for suitable controllable elements allowing for a constitutive expression in eukaryotes are promoters being recognised by RNA polymerase II or viral promoters, CMV-enhancer, CMV-promoter, SV40-promoter or LTR-promoters like e.g. those from MMTV (mouse mammary tumour virus; Lee et al. 1981, Nature 214:228-232) and further viral promoter- and activator sequences, derived e.g. from HBV, HCV, HSV, HPV, EBV, HTLV or HIV. Examples for controllable elements allowing for a scheduled expression in eukaryotes are the tetracycline operator in combination with a respective repressor (Gossen et al. 1994, Curr. Opin. Biotechnol. 5:516-20).

In order to enable the introduction of nucleic acids according to the invention and thus the expression of the polypeptide in a eukaryotic or prokaryotic cell by means of transfection, transformation or infection, the nucleic acid can be present as a plasmid or as a part of a viral or non-viral vector. Particularly suitable as viral vectors are: retroviruses, baculoviruses, vaccinia viruses, adenoviruses, adeno-associated viruses and herpes viruses. Particularly suitable as non-viral vectors are: virosomes, liposomes, cationic lipids or poly-lysine conjugated DNA. Examples for gene therapeutically effective vectors are virus vectors like e.g. adenovirus vectors or retroviral vectors (Lindemann et al., 1997, Mol. Med. 3:466-76; Springer et al. 1998, Mol. Cell. 2:549-58).

A preferred mechanism to accomplish the in vivo expression of the polypeptides according to the invention is the viral gene transfer, in particular by means of retroviral particles. These are preferably employed in order to furnish the respective target cells, preferably T-lymphocytes of the patient ex vivo with the genes or nucleotide sequences coding for polypeptides according to the invention via transduction. The target cells may then be reinfused into the patient in the form of an adoptive cell transfer in order to take over the anti-tumour and/or immunomodulating effector functions introduced together with the de novo specificity. By means of this approach, very good gene therapeutic results were obtained in newborn babies in the treatment of the SCID-X1-disease, which is characterised by immune incompetence. In this treatment, haematological precursor cells were equipped by means of a retroviral transfer with an analogous intact transgene of a non-functional, mutated variant of the χ-chain gene, which in the healthy state is essential for the differentiation of the different effector cells of the adaptive immune system and which occurs in a non-functional variant in these children (Cavazzana-Calvo et al., 2000).

Moreover, there exists the possibility to perform the gene transfer in vivo, on the one hand by preferentially stereotactic injection of the infective particles, on the other hand by the direct application of virus-producing cells (Oldfield et al., Hum. Gen. Ther., 1993, 4:39-69).

The viral vectors commonly used for gene transfer according to the present knowledge mainly are retroviral, lentiviral, adenoviral and adeno-associated viral vectors. These are circular nucleotide sequences derived from natural viruses, wherein at least the genes coding for the viral structural proteins are replaced by the construct to be transferred. New, non-viral vectors consist of autonomous self-integrating DNA-sequences, the transposons, which are introduced e.g. by liposomal transfection into the host cell and which for the first time were successfully employed for the expression of human transgenes in mammalian cells (Yant et al., 2000).

Gene therapeutically effective vectors may also be obtained that way, that one complexes the nucleic acid according to the invention with liposomes, since this allows to achieve a very high efficiency of transfection, in particular in skin cells (Alexander and Akhurst 1995, Hum. Mol. Genet. 4:2279-85). For lipofection, small uni-lamellar vesicles consisting of cationic lipids are produced by an ultrasound treatment of the liposome suspension. The DNA is bound in a ionic manner to the liposome surface, namely in such a relation, that a positive net load remains and 100% of the plasmid DNA is complexed by the liposomes. Besides the lipid mixtures DOTMA (1,2-dioleyloxypropyl-3-trimethyl ammonium bromide) and DPOE (dioleoylphosphatidyl ethanolamine) used by Felgner et al. (1987, supra), numerous novel lipid formulations haven been synthesised since and were tested for their efficiency in the transfection of different cell lines (Behr et al. 1989, Proc. Natl. Acad. Sci. USA 86:6982-6986; Felgner et al. 1994, J. Biol. Chem. 269:2550-25561; Gao and Huang. 1991, Biochim. Biophys. Acta 1189:195-203). Examples for the new lipid formulations are DOTAP N-[1-(2,3-dioleoyloxy)propyl]-N,N,N-trimethylammonium ethyl-sulfate or DOGS (TRANSFECTAM; dioctadecylamidogly-cylspermine). Adjuvants improving the transfer of nucleic acids into the cell may e.g. be proteins or peptides bound to DNA or synthetic peptide-DNA molecules enabling the transport of the nucleic acid into the nucleus of the cell (Schwartz et al. 1999, Gene Therapy 6:282; Brandén et al. 1999, Nature Biotech. 17:784). Adjuvants also comprise molecules enabling the release of nucleic acids into the cytoplasm of the cell (Kiehler et al. 1997, Bioconj. Chem. 8:213) or e.g. liposomes (Uhlmann and Paymann 1990, supra). Another, particularly suitable form of gene therapeutic vectors can be obtained by coating the nucleic acids according to the invention onto gold particles, which then are shot into the tissue, preferably the skin, or into the cells by means of the so-called "gene gun" (Wang et al., 1999, J. Invest. Dermatol. 112:775-81). A further aspect refers to the introduction of "naked DNA" by means of the gene gun, as it is e.g. described in T Niidome and L Huang; Gene Therapy Progress and Prospects: Nonviral vectors; Gene Therapy (2002) 9, 1647-1652 and the references cited therein.

It is of further advantage for the gene therapeutic application of the nucleic acid according to the invention, if the portion of the nucleic acid coding for the polypeptide contains one or more non-coding sequences including intron sequences, wherein these sequences are preferably located between the promoter and the start codon of the polypeptide, and/or a polyA-sequence, especially the naturally occurring polyA-sequence or the SV40 virus polyA-sequence, in particular at the 3'-end of the gene, since this allows for a stabilisation of the mRNA (Jackson 1993, Cell 74:9-14 and Palmiter et al. 1991, Proc Natl. Acad. Sci. USA 88:478-482).

A further aspect of the present invention refers to a recombinant prokaryotic or eukaryotic host organism containing at least one nucleic acid sequence or at least one vector according to the invention. This "host organism" can be or consist in a diploid cell, a plant cell, a mammalian cell, a nematode cell, a fish cell, an insect cell and, in particular, a non-human stem cell. A preferred example would be a mouse stem cell. Moreover, the invention provides a recombinant, non-human organism, in particular a genetically deficient or "knock-out"-mammal (like e.g. a goat or a sheep), -rodent (like e.g. a rabbit, mouse, rat or hamster), -nematode (like *Caenorhabditis elegans*), -fish (like a zebra fish), plant (like *Arabidopsis thaliana*, maize, rice, wheat or potato), insect or jellyfish, in which the respective gene for 7a5/Prognostin has been mutated or deleted. These experimental organisms are valuable "tools" and may e.g. be used in order to screen for binding partners (see e.g. below). Methods for the production of such organisms are familiar to the expert from the respective relevant literature.

A further aspect of the present invention is a polyclonal or monoclonal antibody or an antigen-binding fragment thereof for the diagnosis, prognosis and therapy optimisation in diseases associated with 7a5/Prognostin expression or for the identification of pharmacologically active substances directed to a polypeptide according to the invention and specifically reacting with such a polypeptide, wherein the above mentioned parts of the polypeptide are either immunogenic themselves or may be made immunogenic or may be enhanced in their immunogenic property by coupling them to suitable carriers like e.g. bovine serum albumin. This antibody is either polyclonal or monoclonal; preferably it is a monoclonal antibody. According to the present invention, the term antibody can also subsume genetically produced and potentially modified antibodies or antigen-binding parts thereof, like e.g. chimeric antibodies, humanised antibodies, multifunctional antibodies, bi- or oligospecific antibodies, single-stranded antibodies, F(ab)- or F(ab)$_2$-fragments (see e.g. EP-B1-0 368 684, U.S. Pat. No. 4,816,567, U.S. Pat. No.

4,816,397, WO 88/01649, WO 93/06213, WO 98/24884). The antibodies according to the invention can be used for the diagnosis, therapeutic monitoring and/or treatment of diseases associated with the 7a5/Prognostin-expression or for the identification of pharmacologically active substances. A further aspect refers to the production of antibodies (pAK, mAK) for the evaluation of histological sections.

A further aspect of the invention refers to a method for the production of an antibody, preferably a polyclonal or monoclonal antibody for the diagnosis and/or the treatment of diseases associated with 7a5/Prognostin expression or for the identification of pharmacologically active substances, characterised in that an antibody producing organism is immunised with a polypeptide according to the invention or with functional equivalents thereof or with parts thereof containing at least 6 amino acids, preferably at least 8 amino acids, and in particular at least 12 amino acids or with a nucleic acid according to the invention.

This method is accomplished according to techniques commonly known to the expert by the immunisation of a mammal, e.g. a rabbit, with the polypeptide according to the invention or the mentioned parts thereof or with (a) nucleic acid(s) coding for it, if advantageous in the presence e.g. of Freund's Adjuvant and/or aluminium hydroxide gels (see e.g. Diamond et al. 1981, The New England Journal of Medicine, pp 1344-1349). The polyclonal antibodies generated in the animal in consequence of an immunological reaction can then be easily isolated from the blood by commonly known methods and can be purified e.g. by means of column chromatography. Monoclonal antibodies can e.g. be produced according to the known method described by Winter & Milstein (1991, Nature 349:293-299).

A still further aspect of the present invention refers to a pharmaceutical composition comprising a nucleic acid molecule according to the invention, a polypeptide according to the invention, an oligonucleotide according to the invention or an antibody according to the invention, if appropriate in combination with a pharmaceutically acceptable carrier and/or adjuvant.

The production of pharmaceutical compositions, e.g. in the form of medicines containing nucleic acid molecules according to the invention, a polypeptide according to the invention, oligonucleotides according to the invention or antibodies according to the invention or their employment in the application according to the invention will be accomplished in the traditional form following common pharmaceutical/technical methods. For this aim, the nucleic acid molecules according to the invention, the polypeptide according to the invention, the oligonucleotides according to the invention or an antibody according to the invention are combined with pharmaceutically acceptable adjuvant and carrier substances and are manufactured into medicinal formulations being suitable for the different indications and sites of application.

Thereby, the medicinal products can be produced that way that the respective, desired release rate, e.g. a rapid release and/or a retard or depot effect are realised. Examples for such medicinal products are ointments, gels, plasters, an emulsion, lotion or foam, a cream or mixed-phased or amphiphilic emulsion systems (oil/water- or water/oil-mixed phase), liposome, transfersome, paste or powder.

The term "adjuvant (substance)" according to the invention means any non-toxic, solid or liquid filling material, diluent or packing material, so far as it does not react in an inappropriately adverse manner with a nucleic acid molecule according to the invention, a polypeptide according to the invention, an oligonucleotide according to the invention or an antibody according to the invention or with the patient body. Liquid galenical adjuvants e.g. are sterile water, physiological saline, sugar solutions, ethanol and/or oils. Galenical adjuvants for the production of tablets and capsules can e.g. contain binding agents and filling materials.

Moreover, a nucleic acid molecule according to the invention, a polypeptide according to the invention, an oligonucleotide according to the invention and/or an antibody according to the invention can be employed in the form of systemically applied medicines. These medicines may be parenteralia, to which the injectabilia and the infusions belong to. Injectabilia are produced either in the form of ampoules or as so-called ready-to-use injectabilia, e.g. as ready-to-use syringes or as single-use syringes, but also as a multi-dose injection bottle. The injectabilia can be administered in the form of a subcutaneous (s.c.), intramuscular (i.m.), intravenous (i.v.) or intracutaneous (i.c.) application. In particular, the respective appropriate formulations for injection can be produced as crystal suspensions, solutions, nanoparticulate or colloidally dispersed systems like e.g. hydrosols.

The injectable preparations may further be produced as concentrates, which are dissolved or dispersed in aqueous isotonic diluents. The infusions can as well be prepared as isotonic solutions, fat emulsions, liposome preparations or micro-emulsions. Like injectabilia, also infusion preparations can be produced in the form of concentrates for dilution. The injectable preparations can also be administered in the form of continual infusions both in stationary and ambulant therapy, e.g. in the form of mini-pumps.

The nucleic acid molecule according to the invention, the polypeptide according to the invention, the oligonucleotide according to the invention or an antibody according to the invention can be bound to a micro-carrier or to nanoparticles in the parenteralia, e.g. to micro-dispersed particles on the basis of poly(meth)acrylates, polylactates, polyglycolates, poly-amin acids or polyether urethanes. The parenteral preparations may also be modified as depot preparations, e.g. starting from the "multiple unit principle", if a nucleic acid molecule according to the invention, a polypeptide according to the invention, an oligonucleotide according to the invention or an antibody according to the invention is present in a micro-dispersed, dispersed or suspended form or manufactured into a crystal suspension or starting from the "single unit principle", if a nucleic acid molecule according to the invention, a polypeptide according to the invention, an oligonucleotide according to the invention or an antibody according to the invention is imbedded into a medicinal formulation, e.g. a tablet or a stick, which is implanted in the following. Often, these implants or depot preparations in single unit and multiple unit formulations consist of so-called bio-degradable polymers like e.g. polyesters of the lactic acid or glycolic acid, polyether urethanes, poly-amino acids, poly(meth)acrylates or polysaccharides.

As adjuvant and carrier substances in the preparation of parenteralia one may use aqua sterilisata, substances with pH effects like e.g. organic and inorganic acids and bases and their respective salts, buffer substances for pH adjustment, substances for reaching an isotonic state like e.g. sodium chloride, sodium hydrogencarbonate, glucose and fructose, surfactants or substances with surface activity and emulsifying agents like e.g. partial fatty acid esters of polyoxyethylene sorbitane (Tween®) or e.g. fatty acid esters of polyoxyethylene (Cremophor®), fatty oils like e.g. peanut oil, soybean oil or castor oil, synthetic fatty acid esters like e.g. ethyl oleate, isopropyl myristate or neutral oil (Miglyol®) as well as polymeric adjuvants like e.g. gelatine, dextran, polyvinyl pyrrolidone, additives of organic solvents improving solubility like e.g. propylene glycol, ethanol, N,N-dimethyl acetamide, propylene glycol or complex-forming substances like e.g. citrates and urea, preserving agents like e.g. benzoic acid hydroxypropyl and -methyl esters, benzyl alcohol, antioxidants like e.g. sodium sulphite and stabilising agents like e.g. EDTA.

In suspensions, the addition of thickening agents has the purpose to prevent the settling of the nucleic acid molecules according to the invention, the polypeptides according to the invention, the oligonucleotides according to the invention or an antibody according to the invention; the surfactants and peptisators have the purpose to assure that the sediment can be whirled up; one may furthermore add complex-forming agents like EDTA. One may further produce pharmaceutically active complexes with different polymers, e.g. with polyethylene glycols, polystyrene, carboxymethylcellulose, Pluronics® or polyethylene glycol sorbitol fatty acid esters. For the production of lyophilised preparations one uses builders like mannitol, dextran, saccharose, human albumin, lactose, PVP or gelatine types.

The respective, suitable medicinal formulations can be prepared in accordance with formulas and procedures on the basis of pharmaceutical-physical knowledge, these formulas and procedures being familiar to the expert.

A last aspect refers to the administration of the nucleic acids and/or oligonucleotides according to the invention in gene therapy by means of common transfection systems like e.g. liposomes, "particle gun"-techniques or "gene gun"-techniques with "naked DNA" as already described above.

A further item of the present invention is a host cell, which has been transfected with a vector according to the invention or with another gene construct according to the invention. Host cells may be prokaryotic as well as eukaryotic cells. An example for a prokaryotic host cell is *E. coli*, examples for eukaryotic host cells are *Saccharomyces cerevisiae* and insect cells. Further suitable cells and organisms have already been described above.

A further aspect of the present invention refers to a diagnostic composition comprising a nucleic acid sequence according to the invention, a polypeptide according to the invention, an oligonucleotide according to the invention or an antibody according to the invention. The diagnostic composition according to the invention may also be present as a part of a diagnostic kit of the invention (see below).

A still further aspect of the present invention refers to a method for the diagnosis of tumour diseases comprising the steps of determining the expression of 7a5/Prognostin in a biological sample taken from a pathological tissue and comparison with the expression of 7a5/Prognostin in a healthy tissue. Preferred is the method according to the invention, in which the determination of the expression of 7a5/Prognostin comprises a hybridisation, a PCR, a "real time" (RT)-PCR, an antigen-antibody binding, an ELISA, an optical proteome analysis, a one- or multidimensional gel electrophoresis, an analysis by mass spectrometry, a chromatography, a sequencing procedure, methylation analysis, SNP-determination or combinations of these methods.

Thus, the present invention provides the establishment and application of the transcriptional determination of expression of the 7a5/Prognostin under the employment e.g. (among others) of the real time RT-PCR. As an example, the level of expression of 7a5/Prognostin in the unknown sample (e.g. tumour-RNA) was determined as a percentage of the 7a5/Prognostin-expression in the commercially available human colon carcinoma calibrator cell line SW620.

A further aspect of the present invention refers to a method for the diagnosis of tumour diseases, wherein the tumour disease is metastasising colon cancer. Starting from the information given above one will obtain a prognostic value for the 7a5/Prognostin-expression levels determined according to the way mentioned above, these values serving as clinical parameters. Up to now, there exists no description of a correlation between the expression of the 7a5/Prognostin-transcripts and clinical parameters like metastatic spread and/or metastasis-free survival or general survival. In the case of in vitro-systems, the transfection of the 7a5/Prognostin-cDNA leads to an increased growth and to an increased migration of human colon carcinoma cells. In the in vivo-experiments, enhanced growth characteristics of the transfected cell clones were measured both in the subcutaneous and in the orthotopic animal model. In the orthotropic model, there also occurred a formation of metastases in the liver. The correlation of the expressions of the 7a5/Prognostin transcripts in particular with the prognosis for the distant metastatic spread of the colon carcinomas was unknown up to now and is surprising.

According to the invention, the biological sample to be investigated can be derived from a tumour biopsy from the intestine, liver, lymph nodes, lung, bones or brain. However other biological samples like saliva, urine, blood or parts thereof can also be used.

A further important aspect of the present invention refers to a method for the treatment of tumour diseases, comprising a modulation of the expression of 7a5/Prognostin. The invention relates to the correlation of the (among other factors transcriptional) expression level of 7a5/Prognostin with the organ specificity of metastatic spread and also to the probability of formation of distant metastases in the case e.g. of colon carcinomas. Thus, one is allowed for the potential use of this new gene as a marker gene for tumour diagnostics and, moreover, as an intervention target also for tumour therapy to influence (prevent) the formation of distant metastases e.g. in the colon carcinoma. According to the invention, an approach for the treatment of tumour diseases can comprise the administration of a pharmaceutical composition according to the invention as described above. A further particular aspect of the present invention thus is a method for the treatment of tumour diseases, wherein the tumour disease is metastasising colon cancer.

The identification of the role of 7a5/Prognostin in the metastatic spread in tumour diseases in another aspect of the present invention provides the possibility to use 7a5/Prognostin as a "target" in a method for the detection of substances binding to 7a5/Prognostin. According to the invention, this method comprises contacting a cell expressing 7a5/Prognostin (e.g. a recombinant cell as above) with a candidate substance, the detection of the presence of the candidate substance binding to 7a5/Prognostin, and determination, if the candidate substance also binds to 7a5/Prognostin. Methods for the routine accomplishment of such screenings are familiar to the expert in the pharmaceutical state of the art. By means of "High-Throughput-Technologies" suitable substance libraries can be screened. These libraries and their screening are familiar to the expert and can be readily adapted to the conditions of the present invention without further inventive effort.

Another aspect of the present invention refers to a method for the production of a pharmaceutical composition, comprising the steps of the above mentioned screening method and a suitable formulation of the substance identified in step c) in a pharmaceutically acceptable form.

A further aspect of the present invention relates to the employment of a nucleic acid sequence according to the invention, a polypeptide according to the invention, an oligonucleotide according to the invention or an antibody according to the invention for the diagnosis and/or the treatment of tumour diseases. The respective aspects for this have already been presented above. By starting from the analysis of the changes in the expression of 7a5/Prognostin of a patient, one can moreover determine the pharmacokinetics of the employed therapeutic agent for the treatment and thus modify the treatment parameters in an appropriate manner (wherein the expert is familiar also with other known parameters). This aspect is also known as "personalised medicine". Moreover, it is also possible to attach linkers to items according to the invention for the use in image-based diagnostics or therapy (molecular imaging, directed therapy). These linkers are known to the expert, e.g. from Trail P A, King H D, Dubowchik G M. Monoclonal antibody drug immunoconjugates for targeted treatment of cancer. Cancer Immunol Immunother. May 2003; 52(5):328-37. Epub Jan. 16, 2003; Signore A, Annovazzi A, Chianelli M, Corsetti F, Van de Wiele C, Watherhouse R N. Peptide radiopharmaceuticals for diagnosis and therapy. Eur J Nucl Med. October 2001; 28(10):1555-65. Epub Jul. 31, 2001. Erratum in: Eur J Nucl Med November 2001; 28(11):1737; and Mehvar R. Dextrans for targeted and sustained delivery of therapeutic and imaging agents. J Control Release. Oct. 3, 2000; 69(1):1-25.

A further aspect of the present invention refers to the use of a nucleic acid sequence according to the invention as a marker for human hereditary diseases. For this aim, the sequence of the 7a5/Prognostin is analysed for specific mutations (e.g. SNPs or other point mutations), which may cause different tendencies towards a metastatic spread. It is also possible to use a nucleic acid sequence according to the invention or an oligonucleotide according to the invention for gene therapy. The respective aspects have already been discussed above and also include siRNA and/or antisense techniques.

Finally, the present invention also comprises a diagnostic kit having a diagnostic composition as described above, and, if appropriate, also containing suitable buffers and/or operating instructions. In one embodiment, the diagnostic kit according to the invention is present in the form of a PCR-kit, in particular an RT-PCT-kit or as an ELISA-kit.

One example of such a kit for the "real time" RT-PCR would e.g. be realisable with the primers and probes designed by the inventors for the transcriptional detection of expression of 7a5/Prognostin in combination with all reagents for a real time RT-PCR. Moreover, the inventors have written a reproducible and readily usable working protocol. A further aspect of the invention is the inclusion of 7a5/Prognostin (with using all controls common in this technique) in the DNA chip technology; here both in chips, which—in the respective updated form—comprise "all" known genes, but in particular also in such chips containing in a subject-relevant manner specific genes e.g. of defined tumour entities, signal transduction cascades, etc.

The use of the determination of expression of the herein described, newly identified gene 7a5/Prognostin in the primary tumour in colon carcinoma patients is, among other things, correlated with the formation of distant metastases (e.g. in the liver of lung). The inventors have identified the novel gene 7a5/Prognostin by means of a comparative expression analysis in human primary tumours, metastases of different target organs and the corresponding healthy tissues of colon carcinoma patients. It is localised on chromosome 7 of the human genome.

The transcriptional expression of the 7a5/Prognostin surprisingly is a) higher in the malignant tissues (primary tumours, metastases) than in the corresponding healthy tissues, b) higher in the colon carcinomas' distant metastases, e.g. in the liver and lung, than in the corresponding primary tumour, c) in particular higher in the primary tumours, which have already undergone metastatic spread or will show manifest metastatic spread in the course of the disease than in the primary tumours showing no metastasising behaviour.

Since the herein presented invention of a method for the prognosis concerning the formation of distant metastases in colon carcinoma patients on the basis of the transcriptional detection of the novel gene 7a5/Prognostin focuses on a central clinical issue, an interest in this invention can unrestrictedly be stated for the entirety of all oncologic health centres and research institutes in the world.

In particular, the present invention provides the following advantages:

a) the sequence of the newly identified 7a5/Prognostin-cDNA together with the respective putative protein sequence, wherein characteristic interaction domains are indicated (FIG. 3).

b) in in vitro-systems, the transfection of the 7a5/Prognostin-cDNA leads to an increased growth and to an enhanced migration of the human colon carcinoma cells.

c) in in vivo-experiments both in the subcutaneous and in the orthotopic animal model, enhanced growth characteristics were detected in the transfected cell clones. In the orthotopic model, there moreover resulted a formation of metastases in the liver.

d) determination of the relative 7a5/Prognostin-mRNA expression in primary tumours, metastases and also in the corresponding healthy tissues in colon carcinoma patients.

e) determination of the relative 7a5/Prognostin-mRNA-expression in the primary tumours of colon carcinoma patients.

Since the use of the real time RT-PCR increasingly becomes a "state of the art"-method of transcriptional expression analysis one can increasingly presuppose the necessary device equipment for the application of the invention in laboratories all over the world.

The invention will now in the following be further described in an exemplary manner by referring to the enclosed figures and sequences, in which (in)

Figure 2:
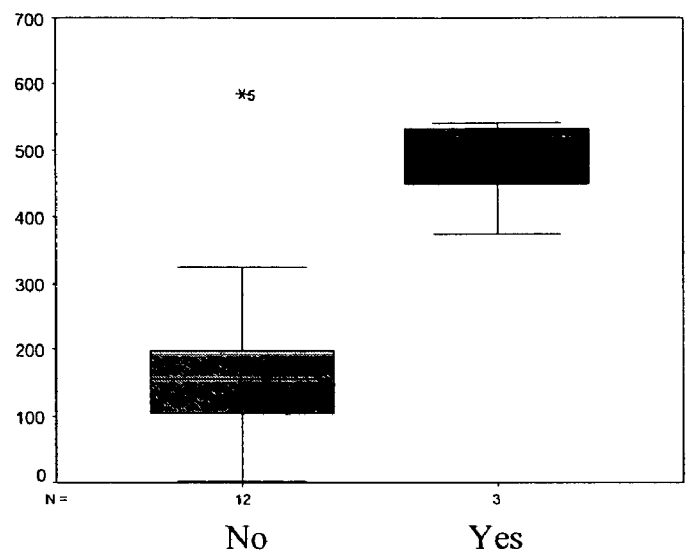
Figure 4:
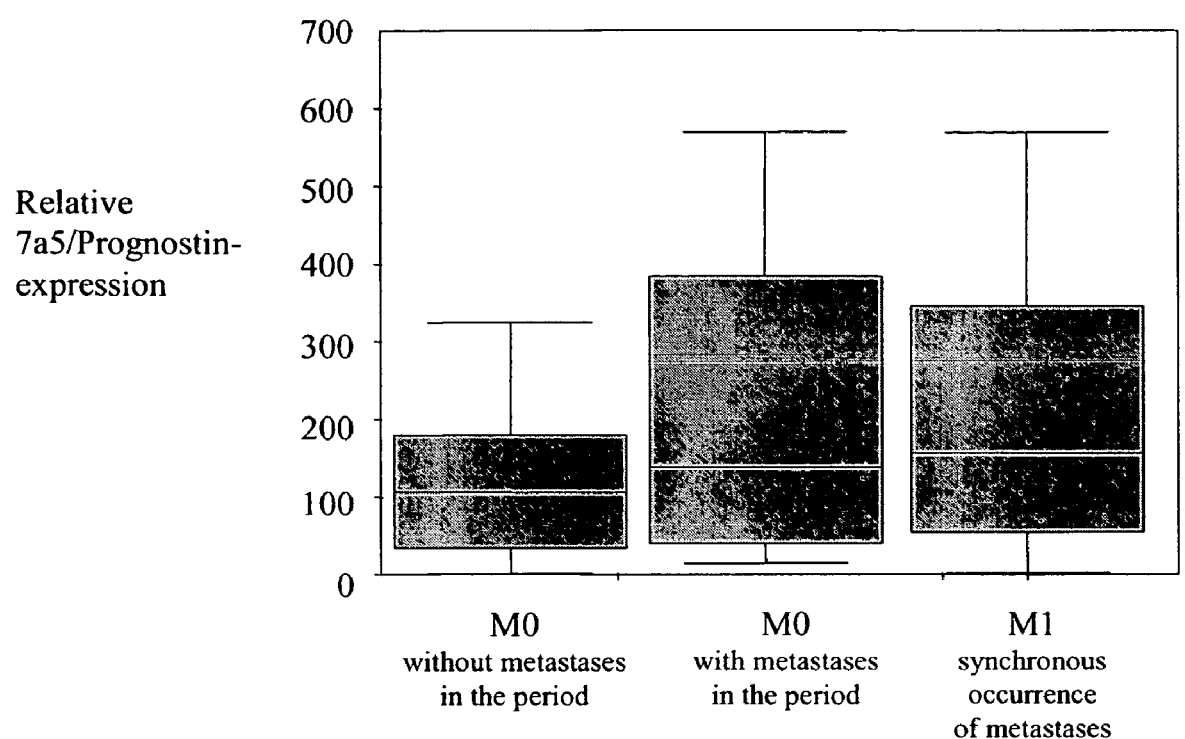
Figure 5:
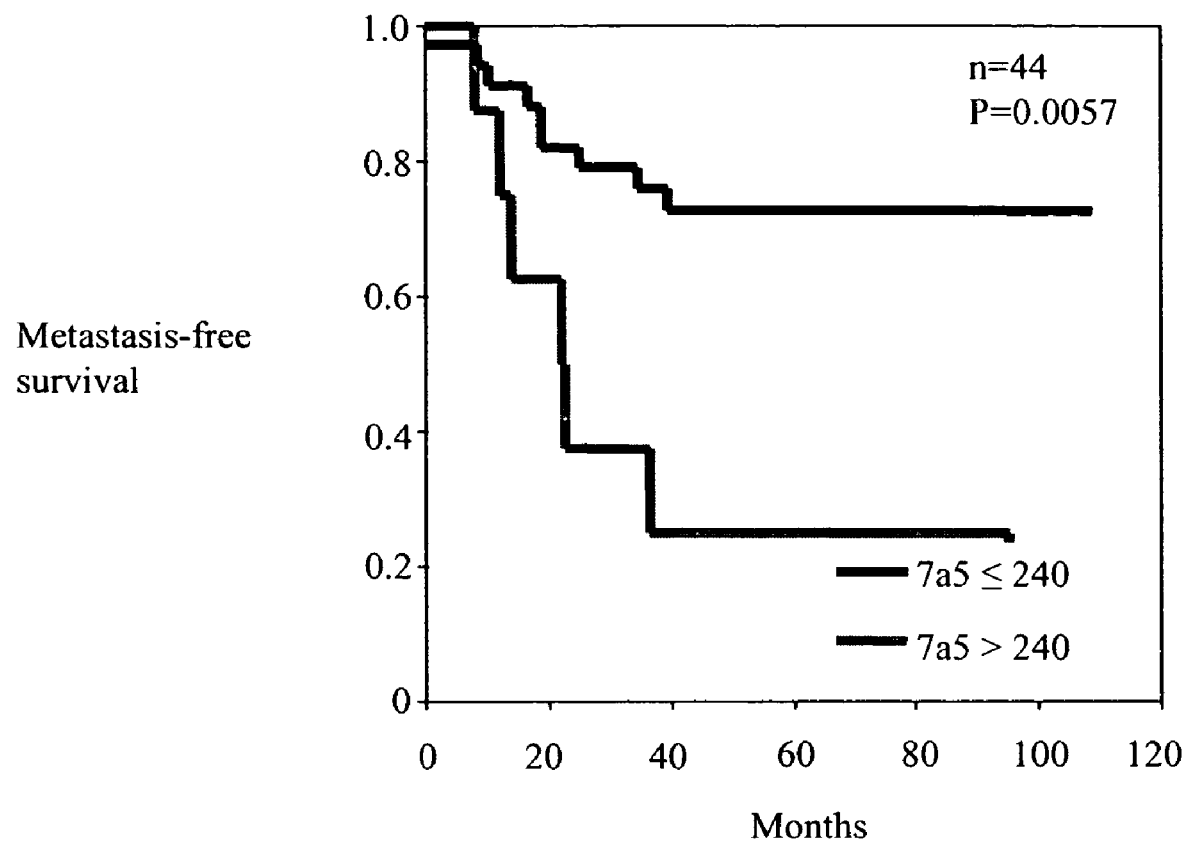

FIG. 1 the relative 7a5/Prognostin-mRNA-expression in primary tumours of colon carcinoma patients correlates with the survival in the metastasis-free state, FIG. 2 the relative 7a5/Prognostin-mRNA expression in primary tumours of colon carcinoma patients correlates with the development of metastases, FIG. 3 shows the sequence of the newly identified 7a5/Prognostin-cDNA [SEQ ID NO: 1] as well as the putative protein sequence [SEQ ID NO: 2]; characteristic interaction domains are indicated, FIG. 4 shows the 7a5/Prognostin-expression in primary tumours of colon carcinoma patients, subdivided into groups according to metastatic spread and time of metastatic spread, FIG. 5 shows the survival of colon carcinoma patients in a metastasis-free state, these patients showing low ($\leq$240) and high (>240) 7a5/Prognostin-expressions in the primary tumours, and FIG. 6 shows the inhibitory influence of 7a5/Prognostin-specific siRNA on the expression of 7a5/Prognostin (A) and the inhibitory influence of 7a5/Prognostin-specific siRNA on the migration behaviour of colon carcinoma cells (B), SEQ ID No. 1: shows the cDNA-sequence of 7a5/Prognostin, SEQ ID No. 2: shows the protein sequence of 7a5/Prognostin, SEQ ID No. 3 to SEQ ID No. 6: show the oligonucleotides used in the examples and SEQ ID No. 7 shows an exemplary siRNA-molecule from the examples.

EXAMPLES

Prognosis of Metastatic Spread Based on the Expression Level of 7a5/Prognostin-mRNA Real Time RT-PCR Patients and Human Tissues 71 patients took part in this study, which was performed under the patients' informed agreement. The human primary colon tumours (46 samples from 44 patients), metastases (52 samples from 41 patients) and healthy tissues (37 mucosa samples, 18 liver tissue samples, 1 lung tissue sample and 1 lymph node; taken from 40 patients) were perioperatively shock frozen in liquid nitrogen and stored for further analyses at −80° C. in the tumour bank of the Robert-Rössle-Klinik, Berlin. The TNM status was determined by pathologists of the Robert-Rössle-Klinik.

Microdissection and RNA Isolation

Serial cryosections of each tissue were prepared for RNA isolation (10 µm) and immunohistochemistry (5 µm). For the micro-dissection of tumour cell populations, every tenth cryosection per tissue was evaluated by a pathologist after staining with haemalaun. Total RNA was isolated from micro-dissection cell populations under the employment of a DNase incubation step (High Pure RNA Tissue Kit, Roche Diagnostics GmbH, Mannheim, Del.). The RNA concentrations were determined in a microplate fluorescence reader (RiboGreen RNA Quantitation Kit, Molecular Probes via MoBiTec, Göttingen, Del.) and were calculated in duplicate preparations from the ribosomal RNA calibrating curves (EasySoftG200/Easy-Fit Software, SLT-Labinstruments, Crailsheim, Del.). The isolation of total RNA from tumour cell lines was performed under the employment of Trizol Reagent (Invitrogen).

Differential Display RT-PCR

Differential display RT-PCR was performed under the employment of the RNAimage Differential Display System 3 (GenHunter Corp., Nashville, Tenn.). Each of the three supplied, one base-anchored primers was used for the reverse transcription of 200 ng total RNA per reaction according to the manufacturer's instruction. The differential display PCR was performed according to the suggested protocol, wherein $\alpha$-[$^{33}$P]dATP (NEN Life Science, Zaventum, Belgium) as a labelling and AmpliTaq polymerase (Applied Biosystems, Weiterstadt, Del.) were used. The PCR-products were separated on a 5% polyacrylamide gel. The gel was blotted, dried and exposed to an X-ray film (Kodak BioMax MR, via Sigmna, Deisenhofen, Del.) overnight. The film was again compared with the gel in order to excise the bands showing different expression. These cDNA-fragments were re-amplified by PCR under the employment of the same primer combinations and PCR conditions as used in the differential display RT-PCR; finally the cDNA-fragments were cloned into the vector pCR2.1 (leading to the constructs described herein: pCR2.1/7a3, pCR2.1/7a5, pCR2.1/7a10, Original TA Cloning Kit, Invitrogen).

Examination of Constructs Containing cDNA-Fragments

The pCR2.1 constructs (herein described: pCR2.1/7a3, pCR2.1/7a5, pCR2.1/7a10) were each blotted onto five nylon membranes under the employment of a Minifold II Slotblot Apparatus (Schleicher & Schuell, Dassel, Del.). Each membrane was hybridised to the complete differential display RT-PCR products being generated from a specific tissue type (Consalez et al. 1996). In order to obtain high specific activity, the differential display RT-PCR products were again labelled with $\alpha$-[$^{32}$P]dCTP (NEN) (Random Primed Labelling Kit, Roche Diagnostics) and were purified (Nucleotide Removal Kit, QIAGEN, Hilden, Del.). The hybridization was performed overnight at 65° C. (6×SSC, 5×Denhardt's Reagent, 0.5% SDS, 100 µg/ml sheared DNA). The blots were exposed to X-ray films (Kodak Xomat-AR). The inserts of constructs showing an expression pattern similar to that found in the differential display RT-PCR were sequenced (Invitek, Berlin, Del.).

cDNA Library Screening

The SW480 cell line-derived human colorectal adenocarcinoma STRETCH PLUS cDNA library (Clontech, Heidelberg, Del.) was transfected into the bacterial host strain Y1090 r⁻. Double filter-replicas were generated under the employment of Optitran strengthened cellulose nitrate membranes (Schleicher & Schuell). The filters were denatured (0.5N NaOH, 1M NaCl) and neutralised (0.5M Tris pH 8, 1M NaCl). The construct pCR2.1/7a5 was labelled with $\alpha$-[$^{32}$P]dCTP (NEN) using the Random Primed Labelling Kit (Roche Diagnostics) and then employed as a probe. The hybridisation was performed over night at 65° C. (5×SSC, 5×Denhardt's Reagent, 0.1% SDS, 100 µg/ml sheared DNA). The filters were then exposed to X-ray films (Kodak Xomat-AR). Positive plaques were picked. The DNA-preparation was performed by means of the Lambda-DNA Preparation Kit (QIAGEN). The cDNA inserts were sequenced (Invitek).

Extension of the Sequence Information

Sequences obtained by the differential display RT-PCR and the cDNA library screening were used for the data base analyses, which were all performed under the employment of the WWW²HUSAR Analysis Package on the server of the biocomputing service group of the DKFZ in Heidelberg. An EST cluster showing sequence identity was determined, this cluster being localised on the genomic DNA sequence fragment AC007001. Three further EST-clusters were localised in the 5'-direction. We performed an EST-linking RT-PCR (GeneAmp RNA PCR Kit, Applied Biosystems) in order to test, if the identified EST-clusters are parts of the 7a5-cDNA. Under the employment of the new sequence information and the cDNA sequence of SH3BP4 showing sequence similarities in overlapping regions, we identified EST-clusters being localised on the genomic DNA sequence fragment AC005083. Long-distance RT-PCR (reverse transcription: Expand Reverse Transcriptase; PCR: Expand High Fidelity PCR, both from Roche Diagnostics) were performed in order to test, if the identified ESTs are parts of the 7a5-cDNA.

5'-RACE

5'-RACE was performed, wherein the SMART RACE cDNA Amplification Kit (Clontech) was used according to the manufacturer's instructions. PCR products separated on agarose gels were re-amplified and cloned in the vector pCR2.1 (Invitrogen) for sequencing.

Cloning of the ORF Into an Expression Vector

Long distance RT-PCR was performed as above, with the exception, that primers for the amplification of the entire ORF without stop codon were used. The primer at the 5'-end was such designed, that a directed cloning of the ORF into the vector pcDNA3.1D/V5-His-TOPO (pcDNA3.1 Directional TOPO Expression Kit, Invitrogen) was allowed in the correct frame. The cloning procedure was performed according to the manufacturer's instructions. The constructs (pcDNA3.1D/ 7a5-V5-His) containing the expected insert, were sequenced.

Generation of Stably Transduced 7a5 Expressing SW480 Cell Clones

In order to analyse the biological function of the 7a5 gene, the 7a5 expressing pcDNA3.1D/7a5-V5-His construct and the LacZ-expressing pcDNA3.1D/V5-His/lacZ-construct (Invitrogen, served as a control) were transduced into SW480 cells under the employment of lipofectin (Invitrogen) according to the manufacturer's instructions. For the transduction of $5 \times 10^4$ cells, 10 µg of plasmid DNA and 15 µl of lipofectin were used. 48 h after transduction, the clones bearing constructs were selected in G418 (Invitrogen) containing medium. After two weeks, colonies became visible, which were then ring-cloned and expanded for further experiments. All isolated cell clones were screened by Western Blots and real time RT-PCR for the expression of 7a5 or LacZ.

Western Blots of 7a5 Expressing SW480 Cell Clones

7a5-transduced, lacZ-transduced and wildtype SW480 cells were lysed in 1% SDS, 10 mM Tris-HCl, 2 mM EDTA and the lysates separated on a 7.5% polyacrylamide gel. After electroblotting (1 h, Trans Blot—Semi Dry Transfer Cell, BioRad, Munich, Del.), expressed 7a5 protein was detected by the employment of an anti-V5 antibody (Invitrogen) and a secondary anti-mouse-HRP antibody (Promega, Madison, Wis.). The chemiluminescence reaction was performed with ECL solution (Amersham Biosciences, Freiburg, Del.) according to the manufacturer's instructions.

Relative Quantitative Two-Step Real Time RT-PCR

The reverse transcriptase reaction (RT) was performed with 50 ng of total RNA (MuLV Reverse Transcriptase, Applied Biosystems). For each quantitative real time PCR (95° C. for 60 seconds, 45 cycles of 95° C. 10 seconds, 60° C. 10 seconds, 72° C. 20 seconds) 1/5 of the RT-volume was taken by using the LightCycler (LightCycler DNA Master Hybridization Probes Kit, Roche Diagnostics). The expression of 7a5 and the house-keeping gene glucose-6-phosphate dehydrogenase (G6PDH) was determined in double preparations from the same RT-reaction. For 7a5, a 136 bp amplicon, and for G6PDH a 136 bp amplicon were produced via primers, which are recognized by gene-specific fluorescin- and LCRed640-labelled hybridisation probes (synthesis of primers and probes: BioTeZ and TIB MolBiol, both Berlin, Del.). The calibrator cDNA was used in parallel in serial dilutions in each run, derived from the cell line SW620.

For the detection of human cell SW620 clone tumours in the mouse liver after orthotopic transplantation, a human satellite sequence was used. Primers (Synthese BioTeZ, Berlin) generating an amplicon, were used (similar to Becker et al., 2002) (Synthesis TIB MolBiol, Berlin). Real time PCR was performed as described above under the employment of 250 ng of genomic DNA.

Primers:

forward:
(SEQ ID No. 3)
5'-ttc ttt tga ttc ctc cgg tga-3' reverse:
(SEQ ID No. 4)
5'-act ctg atg ggc atg tgc tg-3' probes
(here: for the employment with the Light Cycler):

(SEQ ID No. 5)
5'-gca gac ttc ctc aag aaa ttc tgg aag atc ta-3'-FITC

LCRed-
(SEQ ID No. 6)
5'-agt gtt tca gaa ctt ctg gac att tta gac ga-3'

Annealing temperature: 60° C.; number of cycles: 45

Soft Agar Growth of 7a5 Transduced SW480 Tumour Cell Clones

For the evaluation of cell growth in soft agar, 5 ml of 1% Agar (Difco, Detroit, Mich.) preheated to 50° C. were mixed with 5 ml DMEM medium (double concentrated, w/o phenol red, Invitrogen), supplemented with 10% FCS and antibiotics. 200 µl of cell suspension containing $5 \times 10^4$ cells were rapidly added to the 10 ml of the soft agar mixture, mixed thoroughly, poured as 5 ml aliquots into 60 mm Petri dishes and placed on ice for 5 minutes. The 7a5-transduced cell clones, the lacZ-transduced cell clones and the wildtype SW480 cells were then grown in duplicates in soft agar for 8 days and the colonies were counted.

Cell Migration Test

Transwell membrane chambers (pore size 12.0 µm, Costar, Heidelberg, Del.) were equilibrated with 1 ml of RPMI 1640 medium, which was supplemented with 10% FCS for 24 h at 37° C. under 5% of $CO_2$. The medium was then removed and 0.5 ml of cell suspension containing $25 \times 10^5$ cells was added to the filter-membrane chambers and 1.5 ml medium were added to the lower chamber. The number of cells migrating through the membrane into the lower chamber was counted after 24 h of cell inoculation (performed in triplicates).

In Vivo Growth of 7a5 Transduced SW480 Cell Clones: Subcutaneous Transplantation For the in vivo growth of the tumour, $1 \times 10^7$ 7a5-transduced, LacZ-transduced or wildtype SW480 cells were transplanted subcutaneously along the left flank of 6-8 week old male NMRI nu/nu-mice at day 0. Each group of animals comprised 10 animals. The animals were kept for 39 days in order to allow for the development of measurable tumours. The tumour size was measured in two dimensions in all groups at the days 7, 11, 15, 21, 27, 32, 35 and 39. The tumour volumes were calculated as (width$^2$×length)/2 and indicated as the mean tumour volume in cm$^3$. The animals were killed and the tumours withdrawn and shock frozen in liquid nitrogen for further analysis.

In Vivo Growth of 7a5 Transduced SW480 cell Clones: Orthotopic Transplantation $1 \times 10^7$ 7a5-transduced, LacZ-transduced or wildtype SW480 cells were first subcutaneously transplanted along the left flank of 6-8 week old female SCID-beige mice and allowed to grow for three weeks. These tumours were then withdrawn, cut into pieces of 2×1×1 mm$^3$ and transplanted into the caecum of female SCID-beige mice in an orthotopic manner. Each group of animals comprised 5 animal. The animals were kept for 70 days in order to enable tumour growth and metastatic spread. Starting from day 16, the tumour size was measured in all groups one time per week. The animals were killed and both the tumours and the organs potentially being metastatic were withdrawn and shock-frozen in liquid nitrogen for further analyses. After the removal, the final tumour volumes were calculated as length×width× height and indicated as the mean tumour volume in cm$^3$.

In Situ Hybridisation in Human Tissues

For cloning, the 7a5-specific differential display RT-PCR fragment was transferred via pCR2.1/7a5 into the pBluescript II SK+ vector (Stratagene GmbH, Heidelberg, Del.). The in vitro transcription was performed under the employment of T7 and SP6 RNA-polymerases (Epicentre Technologies, Madison, Wis.) in order to obtain sense- and antisense-probes. The transcription was accomplished under the employment of the DIG Labelling Kit (Roche Diagnostics).

Cryosections of human tissues were fixed in paraformaldehyde and dried. The pre-hybridisation was performed for one hour at 55° C. employing 4×SSC, 5% dextran sulfate, 1×Denhardt's Reagent, 50% formamide, 0.25 mg/ml yeast-tRNA and 0.5 mg/ml of fragmented salmon sperm DNA. The hybridisation reaction was performed for 16 h at 55° C. under the employment of the pre-hybridisation solution containing 500 ng/ml of the in vitro-transcribed RNA probe. Extensive washing was performed in 2×SSC, 50% formamide at 55° C. Blocking was accomplished by using "Blocking Reagent" (Roche Diagnostics) according to the manufacturer's instructions. The sections were incubated for two hours with anti-DIG-AP Fab-fragments (Roche Diagnostics). After washing, a colorimetric detection was accomplished under the employment of NBT/BCIP-solution (Roche Diagnostics) and incubation in the dark.

Immunohistochemistry

Cryosections from primary tumours, lymph nodes, pulmonary and liver metastases and also from the respective healthy tissues were immunostained according to a modification of the DAKO catalysed Signal Amplification (CSA) System (DAKO A/S, Glostrup, Denmark): Endogenous biotin reactivity was blocked by means of a UVC-irradiation at 254 nm for 35 minutes at room temperature. The sections were rehydrated in an aqueous 0.01% $NaN_3$ stabiliser solution for 30 minutes at 50° C. Endogenous peroxidase was blocked by incubation with 3% $H_2O_2$ in methanol for 30 minutes at 50° C. The protein block was performed for 5 minutes as recommended.

The primary polyclonal rabbit-anti-human 7a5 antibody was raised against a 7a5-derived polypeptide (AA 812-826, localised near the C-terminus: (KLH)-SALDRMKNPVT-KHWR [SEQ ID NO: 8], Eurogentec, Seraing, Belgium) and was purified by means of affinity chromatography with the peptide antigen coupled to CNBr-sepharose (BioGenes, Berlin, Del.) in the following. This antibody was used for immunohistochemistry in a dilution of 1:1000. In order to avoid the non-specific antibody-based Fc-receptor ligation, an Fc-depleted biotinylated affinity-pure $F(ab')_2$-fragment antibody with anti-rabbit specificity (dilution 1:40,000, Dianova-Jackson ImmunoResearch, Hamburg, Del.) was used. The Streptavidin-HRP was used for 15 minutes at room temperature. The colorimetric detection was performed under the employment of DAB substrate according to the protocol provided by the manufacturer. The nuclei were counterstained with haematoxylin for 1 minute. The sections were analysed according to topographical aspects of expression.

Statistical Analysis

The degree of statistical significance was calculated under the employment of the non-parametric two sided Mann Whitney Rank Sum Test (real-time RT-PCR) and the T-test for two independent samples (growth on soft agar, cell migration test, in vivo growth).

Diagnose on the Basis of 7a5/Prognostin Expression in the Primary Tumours of Colon Carcinoma Patients With and Without Metastatic Spread FIG. 4 (Box plot with indication of the median) shows the degree of 7a5/Prognostin expression in the primary tumours from colon carcinoma patients ($T_{2-4}N_{0-1}$), a) which were not metastasised at the time of the 7a5-analysis and showed no metastatic spread during the observation period of 60 months=M0 without metastases in the period, b) which were not metastasised at the time of the 7a5-analysis, but showed metastatic spread during the observation period of 60 months=M0 with metastases in the period, and c) which at the time of the 7a5-analysis had already formed metastases=M1

In the primary tumours from the patients developing metastases in this period or already showing metastases, significantly higher values for the 7a5/Prognostin expression were measured.

Metastasis-Free Survival in Colon Carcinoma Patients in Dependence on the Level of the 7a5/Prognostin Expression FIG. 5 (Kaplan-Meier-curve) shows the likelihood of metastasis-free survival in dependence on low or high 7a5/Prognostin expression in the respective primary tumour. Calculated as a "cut-off" is a relative 7a5/Prognostin-value of 240, defined as "low" are all relative 7a5/Prognostin-values$\leq 240$ and as "high" all relative 7a5/Prognostin-values$>240$.

Example 1

About 20-25% of the patients with 7a5/Prognostin expressions$\leq 240$ in the primary tumour develop metastases (in the observation period).

Example 2

About 75-80% of the patients with 7a/5Prognostin expressions$>240$ in the primary tumour develop metastases (in the observation period).

The 7a5/Prognostin expression in the primary tumour is significantly predictive for the development of distant metastases (P=0.0057).

Therapeutic Intervention with 7a5/Prognostin Specific siRNA on the Expression Level FIG. 6A describes the influence of transiently transfected, 7a5/Prognostin-specific siRNA-oligonucleotides on the transcriptional expression of 7a5/Prognostin in a stably 7a5/Prognostin-transfected and strongly overexpressing cell clone from a human colon carcinoma cell line. The control not being treated with siRNA corresponds to 100%.

Example for an effective 7a5/Prognostin-specific siRNA-oligonucleotide nt 2233 to 2253 of the full-length cDNA sequence of 7a5/Prognostin 5'-AAGCTTGGAAAAGGCTGGAGG-3'   (SEQ ID No.7)

Intervention With 7a5/Prognostin-Specific siRNA on the Functional Level

FIG. 6B describes the influence of transiently transfected, 7a5/Prognostin-specific siRNA-oligonucleotides on the migration behaviour of a stably 7a5/Prognostin-transfected and strongly overexpressing cell clone from a human colon carcinoma cell line. The control not being treated with siRNA corresponds to 100%. The protocol of the migration assay is to be seen above.

The transient transfection of 7a5/Prognostin-specific siRNA leads to an inhibition of the 7a5/Prognostin expression. The consequence consists in a reduced migration activity of these cells as a biological parameter for the metastasising potential. For the therapeutic application in patients, the 7a5/Prognostin-specific si-RNA oligonucleotides are preferably cloned into respective plasmids. This allows for a stable siRNA-expression in the patient's primary tumour, which in consequence leads to a persistent inhibition of the 7a5/Prognostin expression and can thus reduce metastatic spread.

The invention claimed is:

1. A method for assessing the likelihood of a colon tumour metastasizing, comprising the steps of:
   (a) determining the expression of 7a5/Prognostin in a biological sample from a tissue or a bodily fluid from a patient with a colon tumour; and
   (b) comparing said expression with a control value that is based on the expression of 7a5/Prognostin in non-metastasizing: tumours,
   wherein an elevated 7a5/Prognostin expression in said biological sample compared to the control value indicates a greater likelihood that the colon tumour will metastasize.

2. The method according to claim 1, wherein the determination of said expression of 7a5/Prognostin comprises a hybridisation, a PCR, a "real time" (RT)-PCR, an antigen-antibody binding, an ELISA, an optical proteome analysis, a one- or multi-dimensional gel electrophoresis, an analysis by mass spectrometry, a chromatography, a sequencing procedure, a methylation analysis, a SNP-determination or combination of these methods.

3. The method according to claim 1, wherein said biological sample is derived from a tumour biopsy from the colon or from the bodily fluid of a subject having at least one of said colon tumours.

4. A method for diagnosing whether a subject has cancer, comprising the steps of:
   (a) determining the expression of 7a5/Prognostin in a biological sample from a tissue or bodily fluid of the subject; and
   (b) comparing said expression with a control value that is based on the expression of 7a5/Prognostin in non-cancerous tissue or bodily fluid,
   wherein an elevated 7a5/Prognostin expression in said biological sample compared to the control is indicative of the subject having cancer.

5. The method according to claim 4, wherein the determination of said expression of 7a5/Prognostin comprises a hybridisation, a PCR, a "real time" (RT)-PCR, an antigen-antibody binding, an ELISA, an optical proteome analysis, a one- or multi-dimensional gel electrophoresis, an analysis by mass spectrometry, a chromatography, a sequencing procedure, a methylation analysis, a SNP-determination or combination of these methods.

* * * * *